United States Patent [19]
Pfleiderer et al.

[11] Patent Number: 5,936,077
[45] Date of Patent: Aug. 10, 1999

[54] SOLID PHASE SYNTHESIS OF OLIGONUCLEOTIDES

[75] Inventors: Wolfgang Pfleiderer, Constance; Markus Beier, Mühlacker, both of Germany

[73] Assignee: Hoechst Aktiengesellschaft, Germany

[21] Appl. No.: 08/893,614

[22] Filed: Jul. 11, 1997

[30] Foreign Application Priority Data

Jul. 11, 1996 [DE] Germany ............................ 196 27 898

[51] Int. Cl.$^6$ ........................ C07H 21/00; C07H 21/02; C07H 21/04
[52] U.S. Cl. ........................... 536/23.1; 435/6; 536/25.3; 935/77; 935/78
[58] Field of Search ................. 536/25.3, 23.1; 435/6; 935/77, 78

[56] References Cited

FOREIGN PATENT DOCUMENTS 0 552 766  7/1993  European Pat. Off. .
95 24413   9/1995  WIPO .

OTHER PUBLICATIONS

Sonveaux, "The Organic Chemistry Underlying DNA Synthesis", Bioorganic Chemistry, vol. 14, (1986), pp. 274–325.
Mallams, "Polyethers", Antibiotics (Polyethers), vol. 3, Progress in Medicinal Chemistry, vol. 14, (1977), pp. 47–65.
Castanotto et al., "Biological and Functional Aspects of Catalytic RNAs", Critical Reviews in Eukaryotic Gene Expres., vol. 2, No. 4, (1992), pp. 331–357.
Hendrix et al., "Incorporation of 2'–amino–nucleosides in oligodeox. & oligoribo. as a model for 2'–linked conjugates", Nucleic Acids Rese., vol. 23, No. 1, (1995), pp. 51–57.
Sinha et al., "Labile exocyclic amine protection of nucleosides in DNA, RNA and oligonuc. analog synth. facilitat. N–decaylation, minimizing depurin. & chain degrade.", Biochimi, vol. 75, (1993), pp. 13–23.
Uhlmann et al., "Antisense Oligonulecotides: A New Therapeutic Principle", Chemical Reviews, vol. 90, No. 4, (1980), pp. 542–584.
Kume et al., Cyclic diacyl groups for protection of the N$^6$–amino group of deoxyadenosine in oligodeox. synth. Nucleic Acids Research, vol. 12, No. 22, (1984), pp. 8525–8539.
Beaucage et al., "The Synthesis of Specific Ribonucleotides and Unrelated Phosp. Biomol. Phosphor. Method", Tetrahedron Report No. 345, vol. 49, No. 46, (1993), 10441–10488.
Stengle et al., "Improved Synthesis of Oligodeoxyribonucleotides", Tetrahedron Letters, vol. 31, No. 18, (1990), pp. 2549–2552.
Kamaike et al., "An Efficient Method for the Synthesis of [4–15N]Cytidine and [6–15N] Adeonsine Derivatives from Uridine and Inosine", Tetrahedron Letters, vol. 36, No. 1, (1995), pp. 91–94.

Kume et al., "Further Improvements of Oligodeox. Synth.: Synth. of Tetradeox. on a New Silica Gel Support Using N$^6$–Phtahaloy", The Chemical Society of Japan Chem. Ltrs., (1983), pp. 1597–1600.
Dikshit et al., "Napthaloyl Group: A new selective amino protecting group for deoxynucleosides in oligonucleotide synthesis", Can. J. Chem., vol. 66, (1988), pp. 2989–2994.
Keonig et al., "Perchloric acid in peptide chemistry", Peptides (1990), pp. 143–145.
Kume et al., "Phthaloyl Group: A New Amino Protecting Group of Deoxyadenosine in Oligonucleotide Synthesis", Tetrahedron Ltrs, vol. 23, No. 42, (1982), pp. 4368–1982.
Milligan et al., "Current Concepts in Antisense Drug Design", Journal of Medicinal Chemistry, vol. 36, No. 14, (1993), 1923–1937.
Beck et al., "Applications of Dioxetane Chemiluminescent Probes to Molecular Biology", Anal. Chem., vol. 62, (1990), pp. 2258–2270.
Khorana, "Nucleic Acid Synthesis", Institute for Enzyme Research, (1988), pp. 349–381.
Himmelsbach et al., "The p–Nitrophenylethyl (NPE) Group", Tetrahedron, vol. 40, No. 1, (1984), pp. 59–72.
Vu et al., "Fast Oligonucleotide Deprotection Phosphoramidite Chem. for DNA Synthesis", Tetrahedron Ltr., vol. 31, No. 50, (1990), pp. 7269–7272.
Schulhof et al., "The final deprotection step in oligonucleotide synthesis is reduced to a mild and rapid ammonia treatment by using labile base–portecting groups", Nucleic Acids Res., vol. 15, No. 2, (1987).
Heinzelman, "Annual Reports in Medical Chemistry" vol. 10, (1975), pp. 246–256.
Nucleic Acids Symposium Series No. 11, (1982).
Chaix et al., "3'–3'–Linked Olignucleotiedes: Synthesis and Stability Studies", Biorganic & Medicinal Chemistry ltrs, vol. 6, No. 7, (1996), pp. 827–832.
Kume et al., "Phthaloyl group for protection of the N$^6$–amino group of deoxyadenosine in oligonucleotide synthesis", Nucleic Acids Research, Symposium Series No. 11, (1982), 25–28.
Manoharan, "Designer Antisense Oligonucleotides: Conjugation Chemistry and Functionality Placement", Antisense Research and Applications, (1993), pp. 303–349.

*Primary Examiner*—Ardin H. Marschel
*Attorney, Agent, or Firm*—Foley & Lardner

[57] ABSTRACT

A process is described for preparing oligonucleotides by solid phase synthesis in which exocyclic amino groups present on nucleobases are protected with cyclic diacyl groups, which can be deprotected in the presence of a strong, nonnucleophilic base. Novel intermediates employing the cyclic diacyl protecting groups are also described.

27 Claims, No Drawings

SOLID PHASE SYNTHESIS OF OLIGONUCLEOTIDES

FIELD

The present application relates to solid phase synthesis of oligonucleotides using cyclic diacyl protecting groups.

BACKGROUND

The chemical polycondensation of mononucleotides is an important method for preparing deoxyribonucleic acid (DNA) or ribonucleic acid (RNA).

Oligonucleotides are used to an increasing extent as inhibitors of gene expression (J. F. Milligan, M. D. Matteucci and J. C. Martin, *J. Med Chem.* 36(1993): 1923; E. Uhlmann and A. Peyman, Chemical *Reviews* 90: (1990) 543) or as ribozymes (e.g., D. Castanotto, J. J. Rossi, J. O. Deshler, *Critical Rev. Eukar. Gene Expr.* 2 (1992): 331), or in diagnosis as DNA probes (e.g., Beck und Koester, *Anal. Chem.* 62 (1990): 2258). There is therefore a great need for suitable methods for synthesizing such compounds.

The state of the art with regard to oligonucleotide synthesis is reviewed in E. Sonveaux, *Bioorg. Chem.* 14 (1986): 274; E. Uhlmann and A. Peyman, Chemical *Reviews* 90: (1990) 543, Beaucage and Iyer, *Tetrahedron* 49: (1993) 10441–10488.

A basic problem in the chemical synthesis of DNA or RNA is that of finding suitable protecting groups for the amino and hydroxyl groups of the nucleoside bases and the sugar residues. On the one hand, these protecting groups have to be stable under the conditions of the polycondensation reaction, i.e., during the reaction, and, on the other hand, they have to be sufficiently labile to enable them to be removed again at the end of the reaction without recleaving the phosphodiester bond (H. G. Khorana, *Pure Appl. Chem.* 17 (1968): 349).

Current practice in DNA synthesis essentially provides for three steps: (a) sequential synthesis of the variously protected nucleotides on a solid support; (b) cleavage of the synthesized oligonucleotides from the support; (c) deprotection of the oligonucleotides. While the synthesis of the oligonucleotide on the solid support takes place very rapidly—approximately one hour is required for a 20 mer—and cleavage from the support is also complete within an hour, the final deprotection of the oligonucleotide remains a problem. Standard oligonucleotide synthesis (e.g., M. Reddy, N. B. Hanna, F. Farooqui, WO 95/24413) provides for a treatment of approx. 6 h at 55° C. with conc. $NH_3$ when the conventional benzoyl, for dA and dC, and butyroyl for dG, protecting groups are employed. A whole series of protecting groups which are more sensitive to ammoniacal aminolysis than are the conventionally protected nucleotide derivatives have recently been proposed for speeding up this latter step (M. Reddy et al., see above; Beaucage and Iyer, see above). These protecting groups comprise, for example, the phenoxyacetal group (Schulhof et al., *Nucl. Acids Res.* 15 (1987): 397); the dimethylformamidine group (Vu et al., *Tetrahedron Lett.* 31 (1990): 7269), or the tert-butylphenoxyacetyl group (Sinha et al., *Biochimie* 75 (1993): 13), or phenylacetyl protecting groups as described in Reddy et al. (see above).

While the deprotecting time at 55° C. is reduced to 15–60 minutes when these ammonia-labile protecting groups are employed, their use also suffers from disadvantages. In the first place, the lability of these groups also leads to instability toward the DNA synthesis conditions, for example during the capping step (Beaucage and Iyer, see above). Phenoxyacetyl protecting groups, for example, reduce the solubility of the nucleotide derivatives so that solvent mixtures have to be employed.

An additional criterion for the use of protecting groups for the exocyclic amino functions of the nucleobases is the purity of the resulting products. In the case of deprotecting procedures which use ammonia, and which are carried out after or during cleavage from the support, a mixture of oligonucleotide and eliminated protecting groups is always obtained. The oligonucleotide must then be cleaned up in additional purification steps. Protecting groups which can be eliminated while the oligonucleotide is still on the solid support, without the oligonucleotide being cleaved from the latter, are more advantageous. An example of such a protecting group is the para-nitrophenylethyloxycarbonyl protecting group, which can be removed with DBU while the oligonucleotide is still on the support. Subsequent cleavage of the oligonucleotide from the support with ammonia yields oligonucleotide which is already pure (F. Himmelsbach et al., *Tetrahedron* 40 (1984): 59).

A further criterion for the use of protecting groups for the exocyclic amino functions of the nucleobases is the stability toward acid conditions employed, as a rule, in each reaction cycle for eliminating the 5'-hydroxyl protecting group, for example, 2% dichloroacetic acid in dichloromethane. These conditions lead, particularly in the case of deoxyadenosine, to a not insubstantial degree of depurination. Cyclic diacyl groups, such as phthaloyl or succinoyl groups, were found, when used as protection for the exocyclic amino function, to be particularly stable toward depurination conditions (Kume et al., *Tetrahedron Lett.* 23 (1982): 4365; *Nucleic Acids Res.* 12 (1984): 8525; *Nucleic Acids Res. Symp. Ser.* 11 (1982): 26; *Chemistry Letters* (1983): 1597). However, these groups were also deprotected with ammonia (Kume et al., see above). An example of another cyclic diacyl group is the naphthaloyl group (Dikshit et al., *Can. J. Chem.* 66 (1988): 2989), which is likewise stable toward depurination and was also removed with ammonia.

SUMMARY

It has now been found, surprisingly, that these cyclic diacyl groups are not only particularly stable toward depurination conditions but can be readily eliminated with a strong, nonnucleophilic base such as DBU. This is all the more astonishing since some phthaloyl groups were introduced using DBU—although this was at relatively low DBU concentrations (Kamaike et al., *Tetrahedron Lett.* 36 (1995): 91). Owing to the high stability toward depurination of the nucleobases which are protected with cyclic diacyl groups, and the possibility of readily removing these groups before cleaving the oligonucleotide from the support, these cyclic diacyl groups are ideally suited for use as protecting groups for preparing oligonucleotides.

DETAILED DESCRIPTION

The invention therefore relates to a process for preparing oligonucleotides by means of solid phase synthesis by
  a) sequentially synthesizing the nucleotides on a solid support in accordance with known methods, with exocyclic amino groups which are present on the nucleobases being protected by a cyclic diacyl group making it possible to eliminate any phosphate protecting groups which are present with strong, nonnucleophilic bases,
  b) deprotecting the oligonucleotides which are bound to the solid support, and c) cleaving the deprotected oligonucleotides from the solid support in accordance with known methods, which comprises deprotecting the oligonucleotides which are bound to the solid support in the presence of a strong, nonnucleophilic base in a suitable organic solvent such as acetonitrile, pyridine or N-methylimidazole.

Strong, nonnucleophilic bases, such as DBU (diazabicyclo[5.4.0]undec-7-ene), DABCO (diazabicyclo [2.2.2]octane), DBN (diazabicyclo-[4.3.0]non-5-ene), ethyldiisopropylamine, triethylamine, N-ethylmorpholine, DMAP (dimethylaminopyridine) or lutidine or uncharged, peralkylated polyaminophosphazene bases (R. Schwesinger, *Angew. Chem.* 99 (1987): 1212) are known to those skilled in the art. The strong, nonnucleophilic base DBU is preferred.

Preferably, the deprotection takes place in the presence of a 0.1 to 5 M solution of DBU at from 0 to 70° C. for from 0.1 to 16 h, more preferably in the presence of a 0.3 to 3 M solution of DBU at from 10 to 40° C. for from 0.1 to 2 h, and most preferably in the presence of a 0.5 to 2.5 M solution of DBU at from 20 to 30° C. for from 0.2 to 1.5 h.

The term "oligonucleotides" quite generally encompasses polydeoxyribonucleotides which contain modified and/or unmodified 2'-deoxyribose building blocks (DNA); polyribonucleotides which contain modified and/or unmodified ribose building blocks (RNA); and also other polynucleotides which are synthesized from N-glycosides or C-glycosides of modified and/or unmodified purine or pyrimidine bases, where the phosphate bridges of the polydeoxyribonucleotides, polyribonucleotides or polynucleotides can also exhibit modifications or be replaced with other structures, with the oligonucleotides possessing at least one base having an exocyclic amino group.

Examples of these modifications, which are introduced using methods which are known per se, are:

a) Modifications of the Phosphate Bridge

The following may be mentioned by way of example:

phosphorothioates, phosphorodithioates, methylphosphonates, phosphoramidates, boranophosphates, methyl phosphates, ethyl phosphates and phenyl-phosphonates. Preferred modifications of the phosphate bridge are phosphorothioates, phosphorodithioates and methylphosphonates.

b) Replacement of the Phosphate Bridge

The following may be mentioned by way of example:

replacement with acetamide, formacetal, 3'-thioformacetal, methylhydroxylamine, oxime, methylenedimethylhydrazo, dimethylsulfone and silyl groups. Preference is given to replacement with acetamide, formacetals and 3'-thioformacetals.

c) Modifications of the Sugar

The following may be mentioned by way of example:

β-anomeric sugars, 2'-O-methylribose, O-butylribose, 2'-O-allylribose, 2'-fluoro-2'-deoxyribose, 2'-amino-2'-deoxyribose, p-arabinofuranose and carbocyclic sugar analogs. Modification with 2'-O-methylribose and 2'-O-n-butylribose is preferred. Those modifications are very particularly preferred in which the 2' and 3' carbon atoms of the O-ribose are linked by way of a double bond and in each case carry a hydrogen atom as the substituent.

The novel process is consequently suitable, for example, for preparing compounds of the formula I

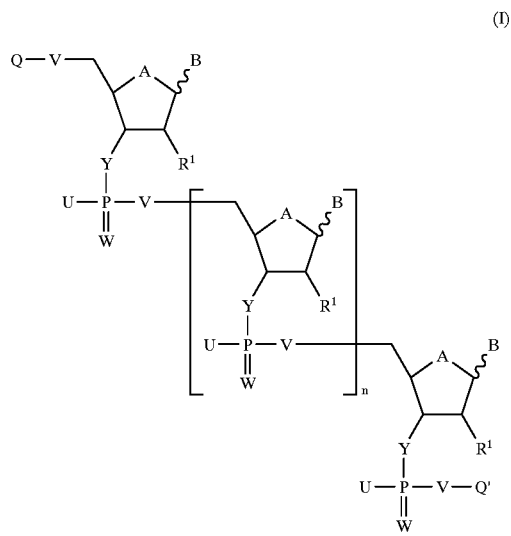

in which $R_1$ is hydrogen, hydroxyl, $C_1$–$C_{18}$-alkoxy, which is optionally substituted one to three times by hydroxyl or $C_1$–$C_4$-alkoxy, $C_1$–$C_4$-alkyl-O-(CH$_2$CH$_2$O)$_s$, in which s is a number from 1 to 3; O-allyl, halogen, azido or amino;

A is, independently in each occurrence, oxy, thioxy or methylene;

W is, independently in each occurrence, oxo, thioxo or selenoxo;

V is, independently in each occurrence, oxy, sulfanediyl or imino;

Y is, independently in each occurrence, oxy, sulfanediyl, imino or methylene;

B is a base customarily employed in nucleotide chemistry, for example natural bases, such as adenine, cytosine, guanine, uracil and thymine, or unnatural bases, such as purine, 2,6-diaminopurine, 7-deazaadenine, 7-deazaguanine, 7-deaza-7-$C_1$–$C_3$-alkynyladenine, 7-deaza-7-$C_1$–$C_3$-alkynylguanine, $N_4N_4$-ethanocytosine, $N_6N_6$-ethano-2,6-diaminopurine, pseudoisocytosine, 5-$C_2$–$C_6$-alkyneuracil, 5-$C_2$–$C_6$-alkynecytosine, preferably 5-propyneuracil, 5-propynecytosine, 5-hexyneuracil, 5-hexynecytosine, 5-fluorocytosine, 5-fluorouracil, 5-hydroxymethyluracil or 5-bromocytosine; with at least one B being a base which possesses an exocyclic amino group;

n is an integer from 1 to 100;

U is hydroxyl, mercapto, BH$_3$, SeH, $C_1$–$C_{18}$-alkoxy, preferably $C_1$–$C_6$-alkoxy, $C_1$–$C_{18}$-alkyl, preferably $C_1$–$C_6$-alkyl, $C_6$–$C_{20}$-aryl, ($C_6$–$C_{14}$)-aryl-($C_1$–$C_8$)-alkyl, NHR$^3$, NR$^3$R$^4$ or a radical of the formula II

in which $R^3$ is $C_1$–$C_{18}$-alkyl, preferably $C_1$–$C_8$-alkyl, $C_6$–$C_{20}$-aryl, ($C_6$–$C_{14}$)-aryl-($C_1$–$C_8$)-alkyl, or —(CH$_2$)$_c$—[NH (CH$_2$)$_c$]$_d$—NR$^5$R$^5$, in which c is an integer from 2 to 6 and d is an integer from 0 to 6;

$R^5$ is, independently in each occurrence, hydrogen, $C_1$–$C_6$-alkyl or $C_1$–$C_4$-alkoxy-$C_1$–$C_6$-alkyl, preferably methoxyethyl;

$R^4$ is $C_1$–$C_{18}$-alkyl, preferably $C_1$–$C_8$-alkyl and particularly preferably $C_1$–$C_4$-alkyl, $C_6$–$C_{20}$-aryl or ($C_6$–$C_{10}$)-aryl-($C_1$–$C_8$)-alkyl, or, in the case of $NR^3R^4$, is, together with $R^3$ and the nitrogen atom carrying them, a 5–6-membered heterocyclic ring which can additionally contain a further heteroatom from the group O, S and N;

p is an integer from 1 to 100, preferably from 3 to 10;

q is an integer from 0 to 22, preferably from 0 to 15;

$R^2$ is hydrogen or a functional group such as hydroxyl, amino, $NHR_6$, COOH, $CONH_2$, $COOR_7$ or halogen, in which $R^6$ is $C_1$–$C_4$-alkyl, and $R^7$ is $C_1$–$C_4$-alkyl, preferably methyl;

Q and Q' are, independently of each other, hydrogen or conjugates which have a favorable effect on the properties of antisense oligonucleotides or of triple helix-forming oligonucleotides (for example, favorable effects on cell penetration, degradation by nucleases, affinity for target RNA/DNA or pharmacokinetics), or are used as the label for a DNA probe, or, in association with the hybridization of the oligonucleotide analog to the target nucleic acid, attack the latter while binding or cross-linking, such as, for example conjugates with polylysine, with intercalators such as pyrene, acridine, phenazine or phenanthridine, with fluorescent compounds such as fluorescein, with cross-linkers such as psoralene or azidoproflavine, with lipophilic molecules such as ($C_{12}$–$C_{20}$)-alkyl, with lipids such as rac-1,2-dihexadecylglycerol, with steroids such as cholesterol or testosterone, with vitamins such as vitamin E, with polyethylene glycol or oligoethylene glycol, with ($C_{12}$–$C_{18}$)-alkyl phosphate diesters, or with —O—$CH_2$—CH(OH)—O—($C_{12}$–$C_{18}$)-alkyl; or, particularly preferably, are conjugates with lipophilic molecules such as ($C_{12}$–$C_{20}$)-alkyl, with steroids such as cholesterol or testosterone, with polyethylene glycol or oligoethylene glycol, with vitamin E, with intercalators such as pyrene, with ($C_{14}$–$C_{18}$)-alkyl phosphate diesters, or with —O—$CH_2$—CH(OH)—O—($C_{12}$–$C_{16}$)-alkyl;

$R^1$ and the adjacent phosphoryl radical can be located either in the 2' and 3' positions or, conversely, in the 3' and 2' positions, wherein each nucleotide may be present in its D or L configuration and the base B may be located in the alpha or beta position, and wherein the oligonucleotide may contain 3'—3' or 5'—5' inversions (Ch. Chaix et al., *Bioorg. & Med. Letters*, 6 (1996): 827); wherein (a) a compound of the formula III

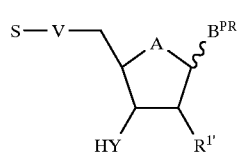

(III)

in which A, Y and V are defined as above, and $R^{1'}$ is defined as $R^1$ where, when $R^1$ is hydroxyl or amino, $R^{1'}$ is a correspondingly protected group;

S is a 5' protecting group which can be eliminated under acid conditions, for example dimethoxytrityl, monomethoxytrityl, trityl or pixyl, preferably dimethoxytrityl and monomethoxytrityl;

$B^{PR}$ is a natural or unnatural nucleobase in which any exocyclic amino groups which may be present are protected by a cyclic diacyl group, is reacted, in accordance with known methods, with a compound of the formula IV

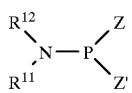

(IV)

in which

Z' is $OR^{13}$ or $C_1$–$C_{18}$-alkyl, $C_1$–$C_{18}$-alkoxy, $C_6$–$C_{20}$-aryl, $C_6$–$C_{14}$-aryl-$C_1$–$C_8$-alkyl, preferably $OR^{13}$, $C_1$–$C_6$-alkyl, $C_1$–$C_6$-alkoxy, $C_6$–$C_{20}$-aryl, or $C_6$–$C_{14}$-aryl-$C_1$–$C_8$-alkyl, particularly preferably $OR^{13}$;

$R^{11}$ and $R^{12}$ are identical or different and are $C_1$–$C_8$-alkyl, preferably isopropyl, or $C_5$–$C_{12}$-cycloalkyl, preferably up to $C_8$, benzyl or phenyl or, together with the nitrogen atom to which they are bonded, a saturated or unsaturated heterocyclic ring optionally having additional heteroatoms, for example morpholine, and substituents, such as OC(O)O—$C_1$–$C_4$-alkyl esters; and $R^{13}$ is a protecting group which can be eliminated with strong, nonnucleophilic bases, Z is chlorine or bromine or a radical of the formula $NR^{11}R^{12}$, where $R^{11}$ and $R^{12}$ are defined as above;

in the presence of a base, preferably pyridine or a mixture of tetrahydrofuran (THF), dioxane, dichloromethane (DCM), chloroform, and/or acetonitrile with a $C_1$–$C_4$-trialkylamine, preferably trimethylamine, triethylamine or diisopropylethylamine, or, when Z is a radical of the formula $NR^{11}R^{12}$, then in the presence of a compound of the formula $[HNR^{14}R^{15}R^{16}]^{(+)} A^{(-)}$, where $R^{14}$, $R^{15}$ and $R^{16}$ are identical or different and are a $C_1$–$C_4$-alkyl group and A is fluorine, chlorine or bromine, in particular chlorine, or tetrazole or 5-($C_1$–$C_4$-alkylthio)-1H-tetrazole, or 5-($C_6$–$C_{12}$)-aryl-1H-tetrazole or other activators, such as pyridine hydrochloride, preferably in the presence of tetrazole or pyridine Hydrochloride, to form a compound of the formula V

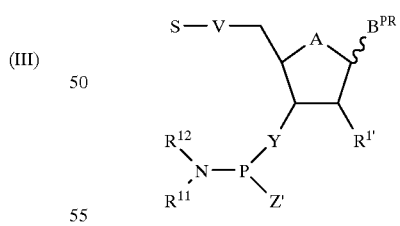

(V)

in which S, V, Y, A, $B^{PR}$, Z', $R^{1'}$, $R^{11}$ and $R^{12}$ are as defined above;

(b) compounds of the formula III are reacted, in accordance with methods known per se, with from 1 to 10 equivalents, preferably with from 1 to 2 equivalents, of a linker, such as succinic anhydride, in a suitable organic solvent, for example methylene chloride, optionally after adding a catalyst, for example 4-dimethylaminopyridine, to give a compound of the formula VI

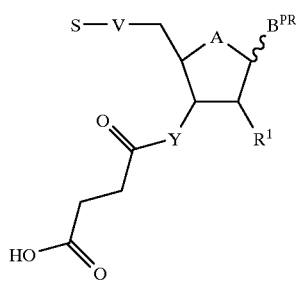

(VI)

where S, V, Y, A, $B^{PR}$ and $R^1$ are as defined above, and subsequently worked up in accordance with methods known per se, such as extraction, crystallization and chromatography, with the succinic acid radical in the 3' position serving as the linker to the polymer support which is employed in the synthesis and wherein other linkers may optionally be used, such as those described in Sonveaux (*Bioorg. Chem.* 14 (1986): 274), as an alternative to the succinic acid linker;

(c) the compound of the formula VI is coupled, in accordance with known methods, to a solid support (SS), such as CPG® (CPG=controlled pore glass) or TENTAGEL®, preferably DBU-stable supports such as "long-chain methylaminoalkyl-CPG" (Stengele, *Tetrahedron Lett.* 1990, 31, 2549), for example by reacting with DCC and p-nitrophenol in a suitable solvent, or by reacting with TOTU (O-[(ethoxycarbonyl)cyanomethyleneamino]-N,N,N',N'-tetramethyluronium tetrafluoroborate: W. König, G. Breipohl, P. Pokorny, M. Birkner, *Proceedings of the 21st European Peptide Symposium* 1990, E. Giralt, D. Andreu, Eds., ESCOM, Leiden, p. 143), where appropriate with the addition of a suitable base such as N-methylmorpholine, N-ethylmorpholine or ethyldiisopropylamine or triethylamine, in a suitable solvent (as described, for example, in M. J. Gait, *Oligonucleotide Synthesis—a practical approach*, IRL Press, 1984), with compounds of the formula VII being obtained:

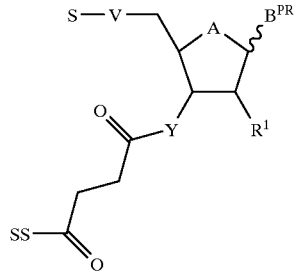

(VII)

(d) the 5' protecting group is eliminated from VII in accordance with methods known per se, for example by treating with 1–4% dichloroacetic or trichloroacetic acid in methylene chloride or chloroform;

(e) the resulting compound is reacted with a compound of the formula V in a suitable organic solvent, preferably acetonitrile, in the presence of a compound of the formula $[HNR^{14}R^{15}R^{16}]^{(+)}$ $A^{(-)}$, which is defined as above, or tetrazole, 5-($C_1$–$C_4$-alkylthio)-1H-tetrazole or 5-($C_6$–$C_{12}$)-aryl-1H-tetrazole, or other activators such as pyridine hydrochloride, preferably in the presence of tetrazole or pyridine hydrochloride, (f) the resulting compound is oxidized in accordance with known methods, for example by reacting with iodine in the presence of aqueous pyridine, lutidine or collidine, optionally also in the presence of additional organic solvents such as tetrahydrofuran, or, for example, by reacting with tert-butyl hydroperoxide in tetrahydrofuran, or by reacting with N,N,N',N'-tetraethylthiuram disulfide in acetonitrile, or, for example, by reacting with iodine in the presence of alkylamine or arylamine, where the different oxidation methods, which are known to a skilled artisan and which are used for preparing natural and modified oligonucleotides, and are summarized, for example, in Beaucage and Lyer (*Tetrahedron* 49(1993): 6123) and also Uhlmann and Peyman (*Chem, Rev.* 90(1990): 543), where the oxidation is preferably carried out by reacting with iodine in the presence of aqueous pyridine, lutidine or collidine, where appropriate also in the presence of additional organic solvents such as tetrahydrofuran;

(f)' unreacted compounds from step (d) are optionally deactivated by means of a capping step, for example by reacting with acetic anhydride-lutidine-N-methylimidazole in THF;

(g) the reaction steps d–f are repeated until the desired chain length has been obtained;

(h) the compound which has been obtained in this way is deprotected by treating with a 0.1 to 5 M solution of DBU in a suitable organic solvent such as acetonitrile, pyridine or N-methylimidazole at from 0 to 70° C. for from 0.1 to 16 h, preferably with an 0.3 to 3 M solution at from 10 to 40° C. for from 0.1 to 2 h, particularly preferably with a 0.5 to 2.5 M solution between 20 and 30° C. for from 0.2 to 1.5 h; and (i) the oligonucleotide is cleaved from the support in accordance with known methods, for example with $NH_3$ at 20–30° C., and the compounds of the formula I are obtained by lyophilizing the ammoniacal solution.

Protecting groups which can be eliminated by strong, nonnucleophilic bases are those protecting groups which are eliminated by treatment with strong, nonnucleophilic bases with the elimination preferably taking place by means of B-elimination. Examples of these protecting groups are 4-nitrophenylethyl, 2-cyanoethyl, dansylsulfonylethyl, arylethyl, and arylsulfonylethyl, where phenyl can optionally be substituted, once or more than once, by chlorine, bromine, CN, $NO_2$, or F, preferably 4-nitrophenylethyl or 2-cyanoethyl.

Compounds of the formula VII can also be synthesized by succinoylating the solid support and subsequently condensing-on compounds of the formula III.

The groups Q and Q' are optionally introduced using methods which are known to the skilled artisan (see, for example, Uhlmann & Peyman, *Chem. Rev.* 90(1990): 543; M. Manoharan in "Antisense Research and Applications", Crooke and Lebleu, Eds., CRC Press, Boca Raton, 1993, Chapter 17, pp. 303 ff. and EP-A 0 552 766).

Protecting groups for $R^{1'}$, when $R^1$ is OH or amino, and the synthesis of correspondingly derivatized nucleoside building blocks, are known to the skilled artisan (such as, for example, the dimethyl-tert-butylsilyl group or the 1-(2- chloro-4-methylphenyl)-4-methoxy-4-piperidinyl group for R¹ is hydroxyl or the acetyl group for R¹ is amino) and are described, for example, in Uhlmann and Peyman, *Chem. Rev.* 90 (1990): 543; Beaucage and Iyer, *Tetrahedron* 48(1993): 2223 or C. Hendrix et al., *Nucl Acids Res.* 26(1995): 51.

Examples of $B^{PR}$ are

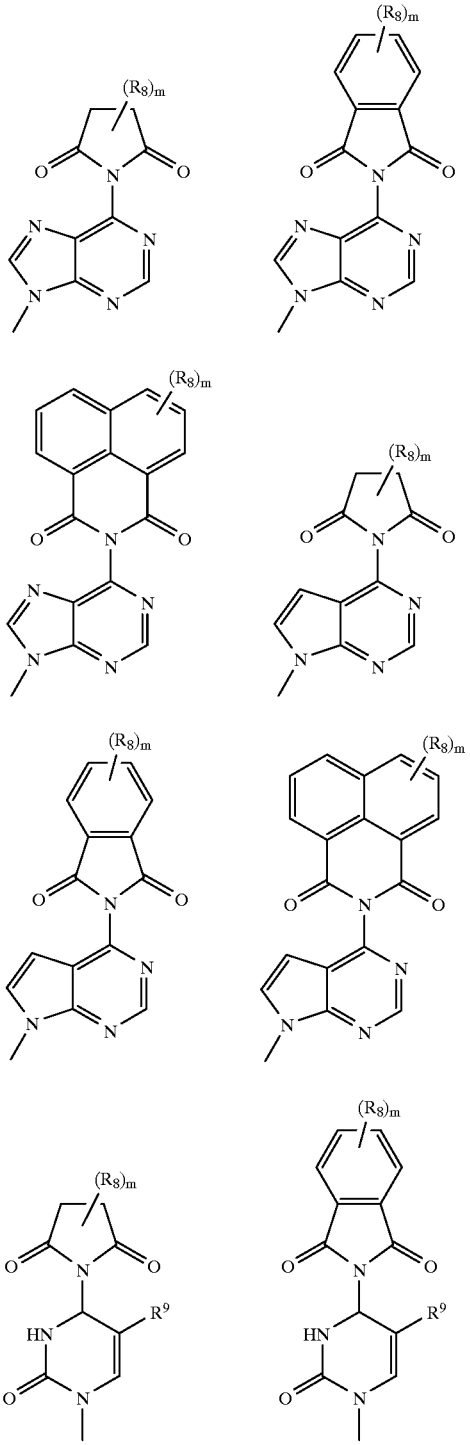
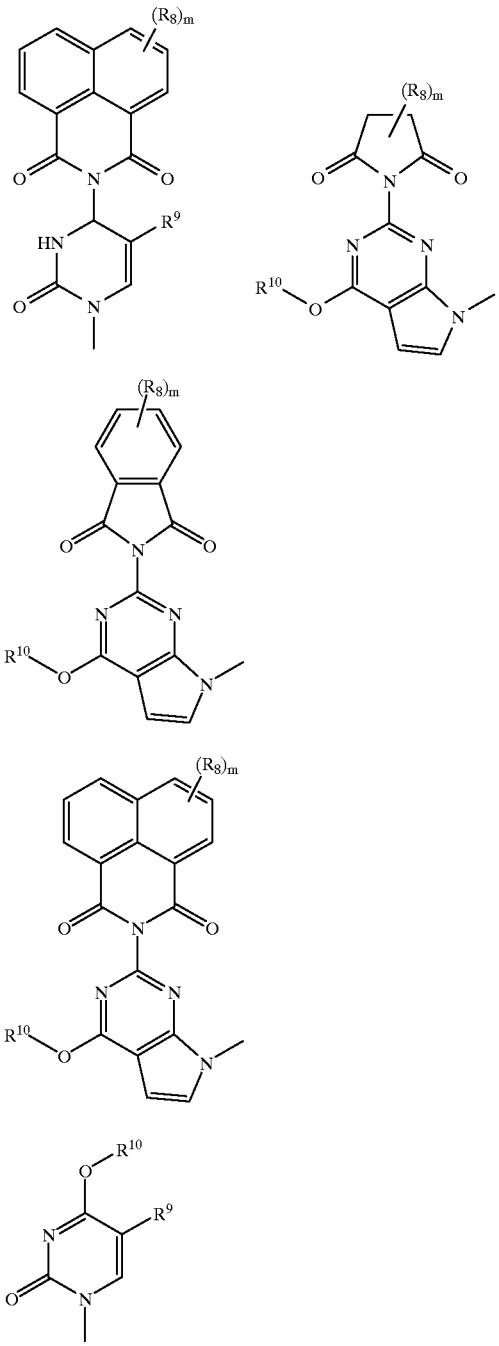

in which
m is a number from zero to four, preferably zero, and
$R^8$ is, independently for each occurrence, hydrogen, fluorine, chlorine, bromine, nitro, $C_1$–$C_4$-alkyl, $C_1$–$C_4$-alkoxy or CN,
$R^9$ is, independently for each occurrence hydrogen, $C_2$–$C_6$-(1-alkyne), preferably 1-propynyl and 1-hexynyl or fluorine; and
$R^{10}$ is, independently for each occurrence, hydrogen or a β-eliminatable protecting group such as para-nitrophenylethyl or phenylsulfonylethyl,
with the introduction into nucleosides of cyclic diacyl protecting groups and the 5' protecting group S being known to the skilled artisan as taught for example by Kume et al., *Tetrahedron Lett.* 23 (1982): 4365; *Nucleic Acids Res.* 12 (1984): 8525; *Nucleic Acids Res. Symp. Ser.* 11 (1982): 26; *Chemistry Letters* 1983, 1597 or Dikshit et al., *Can. J. Chem.* 66 (1988): 2989 or Kamaike et al., *Tetrahedron Lett.* 36 (1995): 91.

Modified nucleoside building blocks can be protected in an analogous manner. The $R^{10}$ protecting groups are likewise introduced, prior to introducing the cyclic diacyl groups, using known methods, for example in accordance with F. Himmelsbach et al., *Tetrahedron* 40 (1984): 59 or Beaucage and Iyer *Tetrahedron* 49 (1993): 6123; Beaucage and Iyer *Tetrahedron* 48 (1993) 2223.

Preference is given to the novel process for preparing compounds of the formula I in which $R^1$ is hydrogen, hydroxyl, $C_1$–$C_4$-alkoxy or fluorine;

A is oxy;

W is oxo or thioxo;

V is oxy;

Y is oxy;

B is, independently for each occurrence, adenine, cytosine, guanine, uracil, thymine, 5-propyneuracil and 5-propynecytosine, 5-hexyneuracil or 5-hexynecytosine, where at least one B is a base which possesses an exocyclic amino group, n is an integer from 5 to 40;

U is hydroxyl, mercapto, $C_1$–$C_6$-alkoxy, $C_1$–$C_6$-alkyl, $NR^3R^4$ or $NHR^3$, in which $R^3$ is $C_1$–$C_8$-alkyl or methoxyethyl;

$R^4$ is $C_1$–$C_8$-alkyl, $C_6$–$C_{20}$-aryl or ($C_6$–$C_{10}$)-aryl-($C_1$–$C_8$)-alkyl, or, in the case of $NR^3R^4$, is, together with $R^3$ and the nitrogen atom carrying them, a 5–6-membered heterocyclic ring which can additionally contain a further heteroatom from the group O, S and N; and Q and Q' are, independently of each other, hydrogen.

Particular preference is given to the novel process for preparing compounds of the formula I in which $R^1$ is hydrogen;

A is oxy;

W is oxo or thioxo;

V is oxy;

Y is oxy;

B is adenine, cytosine, guanine, uracil, thymine, 5-propyneuracil and 5-propynecytosine, 5-hexyneuracil or 5-hexynecytosine;

where at least one B is a base which possesses an exocyclic amino group;

n is preferably from 5 to 30;

U is hydroxyl or $C_1$–$C_6$-alkyl, and

Q and Q' are hydrogen.

The oligonucleotides which are prepared using the novel process can be employed in many different ways, for example as inhibitors of gene expression, as ribozymes or as probes in diagnosis (in particular as DNA probes), or, in a general manner, as aids in molecular biology.

The invention furthermore relates to a compound of the formula V

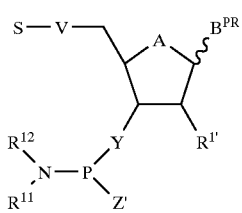

(V)

in which $R^{1'}$ is, independently in each occurrence, hydrogen, $C_1$–$C_{18}$-alkoxy, where appropriate substituted one to three times by hydroxyl, or $C_1$–$C_4$-alkoxy, $C_1$–$C_4$-alkyl-O-$(CH_2CH_2O)_{1-3}$, O-allyl, fluorine, chlorine, azido or a protected hydroxyl or amino group;

A is oxy, thioxy or methylene;

V is oxy, sulfanediyl or imino;

Y is oxy, sulfanediyl, imino or methylene;

S is a 5' protecting group which can be eliminated under acid conditions, for example dimethoxytrityl, monomethoxytrityl, trityl or pixyl, preferably dimethoxytrityl and monomethoxytrityl;

$B^{PR}$ is a natural or unnatural nucleobase having an exocyclic amino group, with the exocyclic amino group (s) being protected by a cyclic diacyl group;

Z' is $OR^{13}$ or $C_1$–$C_{18}$-alkyl, $C_1$–$C_{18}$-alkoxy, $C_6$–$C_{20}$-aryl, or $C_6$–$C_{14}$-aryl-$C_1$–$C_8$-alkyl;

$R^{11}$ and $R^{12}$ are identical or different and are $C_1$–$C_8$-alkyl, preferably isopropyl, or $C_5$–$C_{12}$-cycloalkyl, preferably up to $C_8$, benzyl or phenyl, or, together with the nitrogen atom to which they are bonded, are a saturated or unsaturated heterocyclic ring optionally having additional heteroatoms, for example morpholine, and substituents, such as OC(O)O—$C_1$–$C_4$-alkyl esters; and $R^{13}$ is para-nitrophenylethyl or 2-cyanoethyl.

Preference is given to compounds of the formula V in which $B^{PR}$ is

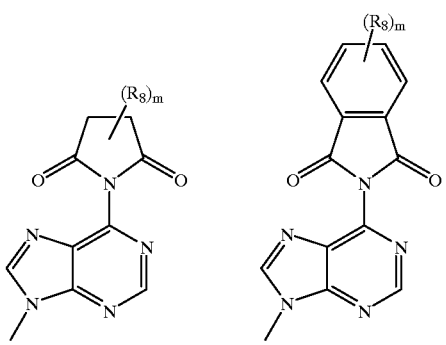

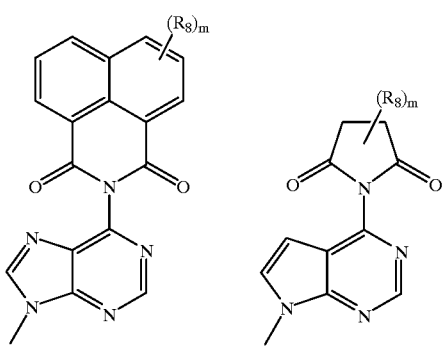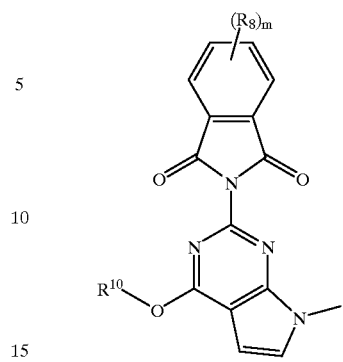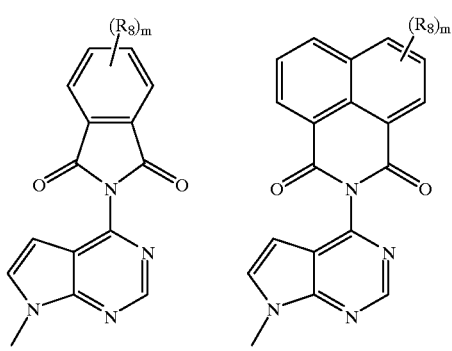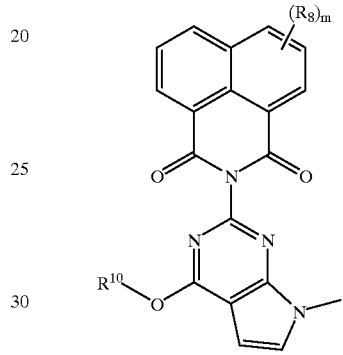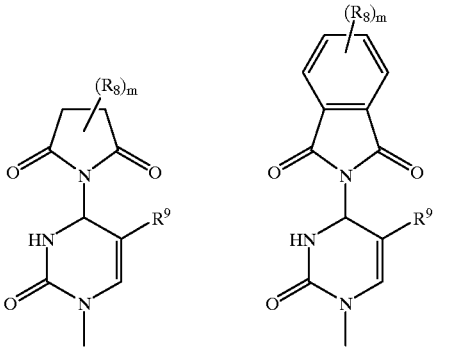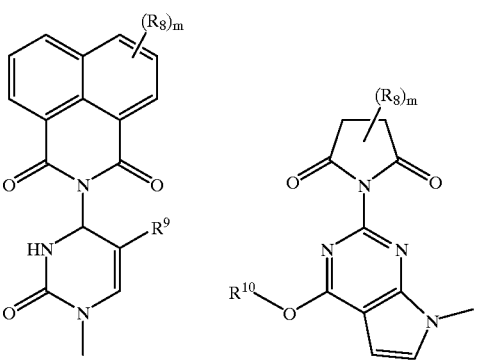

in which
m is a number from zero to four, preferably zero; and
$R^8$ is, independently of each other, hydrogen, fluorine, chlorine, bromine, nitro, $C_1$–$C_4$-alkyl, $C_1$–$C_4$-alkoxy, or CN;

Particular preference is given to compounds of formula V in which
$R^{1'}$ is hydrogen, a protected hydroxyl group, $C_1$–$C_4$-alkoxy or fluorine,
A is oxy;
V is oxy;
Y is oxy;
Z' is $OR^{13}$, $C_1$–$C_6$-alkyl, $C_1$–$C_6$-alkoxy, $C_6$–$C_{20}$-aryl, or $C_6$–$C_{14}$-aryl-$C_1$–$C_8$-alkyl, preferably $OR^{13}$.

The compounds of the formula V are useful intermediates for the preparation, according to the invention, of the compounds of the formula I.

The invention is further illustrated by, though in no way limited to, the following examples:

EXAMPLE 1

5'-O-Dimethoxytrityl-$N^6$-phthaloyl-2'-O-deoxyadenosine-3'-O-(N,N-diisopropyl[2-(4-nitrophenyl)ethyl])phosphitamide 1.1 $N^6$-Phthaloyl-2'-O-deoxyadenosine 5 g of 2'-O-desoxyadenosine (20 mmol) are first coevaporated in absolute pyridine and then dissolved in 80 ml of pyridine; 6 ml of chlorotrimethylsilane (50 mmol) are added and the whole is stirred at room temperature (RT) for 30 min. 4 ml of phthaloyl chloride (28 mmol) are then added. After 2 hr, hydrolysis takes place using ice water and the mixture is subsequently stirred for 10 min. It is diluted with 150 ml of AcOEt and extracted four times with 100 ml of a saturated solution of sodium chloride; the aqueous phase is then back-extracted four times with 50 ml of AcOEt. For purification, the residue is taken up in 50 ml of dichloromethane and precipitation takes place from 1000 ml of petroleum ether. 7.37 g (18.5 mmol; 93%) of an ocher-colored solid are obtained.

1.2 5'-O-Dimethoxytrityl-N$^6$-phthaloyl-2'-O-deoxyadenosine (Literature: Akiko Kume, Mitsuo Sekine, Tsujiaki Hata, *Tetrahedron Letters* 23(42): 4365–4368 (1982))

4 g of N$^6$-phthaloyl-2'-O-deoxyadenosine (10 mmol) are coevaporated with absolute pyridine, then dissolved in 50 ml of absolute pyridine and 50 ml of dichloromethane with 20 mg of N,N-dimethylaminopyridine (0.16 mmol) and a 4 Å molecular sieve are stirred, for 2.5 hr, with 2.72 g of 4,4-dimethoxytrityl chloride (8 mmol). After stripping off the solvent, the residue is dissolved in 100 ml of dichloromethane and this solution is extracted with 100 ml of a solution of sodium hydrogen carbonate. The combined organic phases are dried over magnesium sulfate. They are then filtered and subjected to rotary evaporation and the residue is coevaporated with toluene. The product is then chromatographed on silica gel (100 g) using a toluene/AcOEt gradient (44–80% AcOEt). 3.12 g (4.56 mmol; 46%) of a white foam result.

1.3 5'-O-Dimethoxytrityl-N$^6$-phthaloyl-2'-O-deoxyadenosine-3'-O-(N,N-diisopropyl[2-(4-nitrophenyl)ethyl])phosphitamide 400 mg of 5'-O-dimethoxytrityl-N$^6$-phthaloyl-2'-deoxyadenosine (0.58 mmol) are dissolved in 5 ml of acetonitrile, and 313 mg of bis(N,N-diisopropylamino)-2-(4-nitrophenyl)ethoxyphosphane (0.79 mmol) and 20 mg tetrazole (0.29 mmol) are added. After stirring for 1 hr, the mixture is subjected to rotary evaporation under a protective gas and the residue is dissolved in 50 ml of dichloromethane; this solution is extracted with 50 ml of a saturated solution of sodium hydrogen carbonate. After having been dried over MgSO$_4$, it is subjected to rotary evaporation. The residue is chromatographed on silica gel (6 g of SiO$_2$) using toluene/AcOEt (1:1), and 380 mg (0.39 mmol; 67%) of a white foam are obtained.

TLC (silica gel): R$_f$=0.79 (toluene/AcOEt 1:9)); $^1$H-NMR (DMSO, 250 MHZ): 8.91 (s, 1H, H—C(2)), 8.80 (s, 1H, H—C(8)), 8.07 (m, 6H, 4H pth, 2 H o to NO$_2$), 7.46 (d, 2H, 2H m to NO$_2$), 7.16 (m, 9H, DMTr), 6.80 (m, 4H, o to OCH$_3$), 6.51 (t, 1H, H—C(1')), 4.75 (m, 1H, H—C(3')), 4.13 (m, 1H, H—C(4')), 3.75 (m, 8H, CH$_2$O, 2× O—CH$^3$), 3.50 (m, 2H, H—C(5'), H—C(5")), 3.20 (m, 6H, CH$_2$-phenyl, 2× N—CH, H—C(2'), H—C(2")), 1.01 (m, 12 H, 2× C(CH$_3$)$_2$); $^{31}$P-NMR (DMSO, 161.7 MHZ): 1s 147.50; C$_{53}$H$_{54}$N$_7$O$_{10}$P$_1$ (980.04); calc.: C, 64.95, H, 5.55, N, 10.00; found: C, 64.15, H, 5.53, N, 9.72.

EXAMPLE 2

5'-O-Dimethoxytrityl-N$^6$-phthaloyl-2'-O-deoxyadenosine-3'-O-(β-cyanoethyl-N,N-diisopropyl)phosphitamide 500 mg of 5'-O-dimethoxytrityl-N$^6$-phthaloyl-2'-deoxyadenosine (Example 1.2) (0.73 mmol) are dissolved in 5 ml of acetonitrile, and 280 mg of bis-(N,N-diisopropylamino)-2-cyanoethoxyphosphane (0.92 mmol) and 26 mg of tetrazole (0.37 mmol) are added. After the mixture has been stirred for 1.5 hr under a protective gas, it is extracted with 70 ml of dichloromethane and 60 ml of a solution of sodium hydrogen carbonate. After having been dried over MgSO$_4$, it is subjected to rotary evaporation. The residue is chromatographed on silica gel (9 g of SiO$_2$) in a toluene/AcOEt gradient (40–50% AcOEt), and 430 mg (0.49 mmol; 67%) of a white foam are obtained.

TLC (silica gel): R$_f$=0.33/0.42 (toluene/AcOEt 1:1)); $^1$H-NMR (DMSO, 250 MHZ): 8.92 (s, 1H, H—C(2)), 8.82 (s, 1H, H—C(8)), 8.09 (m, 4H, pth), 7.33 (m, 2H, DMTr), 7.21 (m, 7H, DMTr), 6.82 (m, 4H, o to OCH$_3$), 6.55 (m, 1H, H—C(1')), 4.82 (m, 1H, H—C(3')), 4.27 (m, 1H, H—C(4')), 3.65 (m, 10H, CH$_2$O, 2× O—CH$_3$, H—C(5'), H—C(5")), 3.20 (m, 4H, 2× N—CH, H—C(2'), H—C(2' )), 1.10 (m, 12 H, 2× C(CH$_3$)$_2$); $^{31}$P-NMR (DMSO, 161.7 MHZ): 2s 148.51/147.99; C$_{48}$H$_{50}$N$_7$O$_8$P$_1$ (883.95); calc.: C, 65.22, H, 5.70, N, 11.09 ; found: C, 64.94, H, 5.78, N, 10.87.

EXAMPLE 3

5'-O-Dimethoxytrityl-N$^6$-phthaloyl-2'-O-deoxycytidine-3'-O-(β-cyanoethyl-N,N-diisopropyl)phosphitamide 3.1 N$^6$-Phthaloyl-2'-O-deoxycytidine The synthesis is effected in accordance with Example 1.1: 5.8 g of 2'-O-deoxycytidine (22 mmol) are stirred in 80 ml of pyridine together with 7 ml of chlorotrimethylsilane (55 mmol) and, after 1 hr, 4.4 ml of phthaloyl chloride (33 mmol) in 10 ml of dry dioxane are added dropwise within a period of 60 min. 50 mg of DMAP are added and the reaction is stopped with water after 45 min; the mixture is then stirred for a further 15 min. The mixture is extracted with 10% pyridine in dichloromethane and 100 ml of water. The organic phase is washed with 100 ml of water and the aqueous phase is back-extracted twice with 50 ml of 10% pyridine in dichloromethane on each occasion. After drying and rotary evaporation, and coevaporation of the residue with toluene, the residue is slurried in dichloromethane and filtered off with suction. 5.07 g (14.2 mmol; 64%) of an ocher-colored powder result.

TLC (silica gel): R$_f$=0.10 (toluene/AcOEt/MeOH 5:4:1)); $^1$H-NMR (DMSO, 250 MHZ): 8.63 (d, 1H, H—C(6)), 8.01 (m, 4H, pth), 6.69 (d, 1H, H—C(5)), 6.10 (t, 1H, H—C(1')), 5.30 (d, 1H, HO—C(3')), 5.11 (t, 1H, HO—C(5')), 4.23 (m, 1H, H—C(3')), 3.91 (m, 1H, H—C(4')), 3.63 (m, 2H, H—C(5'), H—C(5")), 2.38 (m, 1H, H—C(2')), 2.14 (m, 1H, H—C(2")); UV (ACN): pmax (nm)/log p: [331/3.68], 316/3.80, [306/3.79], 218/4.51;

C$_{17}$H$_{15}$N$_3$O$_6$ (357.32); calc.: C, 57.14, H, 4.23, N, 11.76; found: C, 57.21, H, 4.45, N, 11.66.

3.2 5'-O-Dimethoxytrityl-N$^6$-phthaloyl-2'-O-deoxycytidine

The synthesis is effected in accordance with Example 1.2: 3 g of N$^6$-phthaloyl-2'-O-deoxycytidine (8.39 mmol) in 60 ml of pyridine together with 50 mg of N,N-dimethylaminopyridine (0.41 mmol) and a 4 Å molecular sieve are stirred for 2 hr with 3.13 g of 4,4-dimethoxytrityl chloride (9.23 mmol). After extracting with 100 ml of dichloromethane and 100 ml of a solution of sodium hydrogen carbonate, chromatography takes place on silica gel (75 g) using a toluene/AcOEt gradient (33–75% AcOEt). 3.35 g (5.10 mmol; 61%) of a white foam result.

TLC (silica gel): R$_f$=0.39 (toluene/AcOEt/MeOH 5:4:1)); $^1$H-NMR (DMSO, 250 MHZ): 8.42 (d, 1H, H—C(6)), 7.99 (m, 4H, pth), 7.30 (m, 9H, DMTr), 6.92 (m, 4H, o to OCH$_3$), 6.53 (d, 1H, H—C(5)), 6.11 (t, 1H, H—C(1')), 5.40 (d, 1H, HO—C(3')), 4.31 (m, 1H, H—C(3')), 4.01 (m, 1H, H—C(4')), 3.73 (s, 6H, 2× O—CH$_3$), 3.33 (m, 2H, H—C(5'), H—C(5")), 2.40 (m, 1H, H—C(2')), 2.20 (m, 1H, H—C (2")); UV (ACN): pmax (nm)/log p: [331/3.68], 317/3.84, [306/3.83], 283/3.72, [275/3.69], 232/4.65; $C_{38}H_{33}N_3O_8$ (659.70); calc.: C, 69.19, H, 5.04, N, 6.37; found: C, 69.29, H, 5.35, N, 6.17.

3.3 5'-O-Dimethoxytrityl-N$^6$-phthaloyl-2'-O-deoxycytidine-3'-O-(β-cyanoethyl-N,N-diisopropyl)phosphitamide The synthesis is effected in accordance with Example 2: 660 mg of 5'-O-dimethoxytrityl-N$^6$-phthaloyl-2'-deoxycytidine (1 mmol) are dissolved in 7 ml of acetonitrile, and 362 mg of bis-(N,N-diisopropylamino)-2-cyanoethoxyphosphane (1.2 mmol) and 35 mg of tetrazole (0.5 mmol) are added. After 1.5 hr, extraction takes place with 100 ml of dichloromethane and 60 ml of a solution of sodium hydrogen carbonate. Chromatography takes place on silica gel (8 g of $SiO_2$) in a toluene/AcOEt gradient (40–50% AcOEt), and 620 mg (0.72 mmol; 72%) of a white foam are obtained.

TLC (silica gel): $R_f$=0.47/0.51 (toluene/AcOEt 1:6); $^1$H-NMR (DMSO, 250 MHZ): 8.45 (m, 1H, H—C(6)), 7.99 (m, 4H, pth), 7.30 (m, 9H, DMTr), 6.91 (m, 4H, o to $OCH_3$), 6.55 (d, 1H, H—C(5)), 6.15 (m, 1H, H—C(1')), 4.52 (m, 1H, H—C(3')), 4.17 (m, 1H, H—C(4')), 3.72 (s, 6H, 2× O—$CH_3$), 3.60 (m, 6H, H—C(5'), H—C(5"), $CH_2$O, 2× N—CH)), 2.70 (2t, 2H, $CH_2$CN), 2.60 (m, 1H, H—C(2')), 2.40 (m, 1H, H—C(2")), 0.97–1.19 (m, 12 H, 2× $C(CH_3)_2$). $^{31}$P-NMR (DMSO, 161.7 MHZ): 2s 148.63/148.38; $C_{47}H_{50}N_5O_8P_1$ (859.91); calc.: C, 65.65, H, 5.86, N, 8.14; found: C, 64.16, H, 6.04, N, 8.23.

EXAMPLE 4

5'-O-Dimethoxytrityl-O$^6$-[2-(4-nitrophenyl)ethyl]-N$^2$-phthaloyl-2'-deoxyguanosine-3'-O-(cyanoethyl-N,N-diisopropyl)phosphitamide 4.1 O$^6$-[2-(4-Nitrophenyl)ethyl]-N$^2$-phthaloyl-2'-deoxyguanosine The synthesis is effected in accordance with Example 1.1.

Variation A: Elimination of the Trimethylsilyl Groups With Pyridine/Water 833 mg of O$^6$-[2-(4-nitrophenyl)ethyl]-2'-deoxyguanosine (2 mmol) are stirred together with 0.63 ml of chlorotrimethylsilane (5 mmol) in 15 ml of pyridine and, after 30 min, 0.43 ml of phthaloyl chloride (3 mmol) in 5 ml of dry dioxane are added dropwise within a period of 15 min. After 2 hr, the reaction is stopped with water and the mixture is then stirred for a further 15 min. The mixture is extracted twice with 50 ml of a solution of sodium hydrogen carbonate and 50 ml of dichloromethane, and the aqueous phases are extracted once again with 50 ml of dichloromethane. The organic phase is dried over $MgSO_4$, filtered and concentrated. The residue is purified on a silica gel column (25 g of $SiO_2$) by means of flash chromatography in a toluene/AcOEt (5:4)-MeOH gradient (0–5% MeOH). 0.56 g (1.02 mmol; 51%) of a slightly yellowish foam is obtained.

Variation B: Elimination of the Trimethylsilyl Groups With Ammonium Fluoride 833 mg of O$^6$-[2-(4-nitrophenyl)ethyl]-2'-deoxyguanosine (2 mmol) are stirred together with 0.63 ml of chlorotrimethylsilane (5 mmol) in 15 ml of pyridine and, after 30 min, 0.57 ml of phthaloyl chloride (4 mmol) in 2 ml of dry dioxane is added dropwise within a period of 5 min. After 2 hr, the mixture is subjected to rotary evaporation and the residue is coevaporated with toluene and then treated with 160 mg of ammonium fluoride (4.3 mmol) in 20 ml of MeOH. The mixture is stirred for 3 min and then extracted twice with 100 ml of a solution of sodium hydrogen carbonate and 100 ml of dichloromethane, and the aqueous phases are extracted once again with 50 ml of dichloromethane. Purification is effected on a -silica gel column (25 g of $SiO_2$) by means of flash chromatography in a toluene/AcOEt (5:4)-MeOH gradient (0–5% MeOH). 0.45 g (0.82 mmol; 41%) of a slightly yellowish foam is obtained.

Variation C: Elimination of the Trimethylsilyl Groups With Tetrabutylammonium Fluoride 833 mg of O$^6$-[2-(4-nitrophenyl)ethyl]-2'-deoxyguanosine (2 mmol) are stirred together with 0.7 ml of chlorotrimethylsilane (5.5 mmol) in 15 ml of pyridine and, after 30 min, 0.55 ml of phthaloyl chloride (3.8 mmol) in 3 ml of dry dioxane is added dropwise within a period of 10 min. After 2 hr, 1.26 g of tetrabutylammonium fluoride trihydrate (4 mmol) are added and the mixture is stirred for 5 min. It is subsequently extracted twice with 100 ml of a solution of sodium hydrogen carbonate and 100 ml of dichloromethane, and the aqueous phases are extracted once again with 50 ml of dichloromethane. Purification is effected on a silica gel column (25 g of $SiO_2$) by means of flash chromatography in a toluene/AcOEt (5:4)-MeOH gradient (0–5% MeOH). 0.39 g (0.71 mmol; 36%) of a slightly yellowish foam is obtained.

TLC (silica gel): $R_f$=0.42 (chloroform/methanol 9:1); $^1$H-NMR (DMSO, 250 MHZ): 8.71 (s, 1H, H—C(8)), 8.14 (d, 2H, 2H o to $NO_2$), 8.00 (m, 4H, pth), 7.61 (d, 2H, 2H m to $NO_2$), 6.39 (t, 1H, H—C(1')), 5.32 (d, 1H, HO—C(3')), 4.91 (t, 1H, HO—C(5')), 4.83 (t, 2H, $CH_2$O), 4.40 (m, 1H, H—C(3')), 3.85 (m, 1H, H—C(41)), 3.51–3.58 (m, 2H, H—C(5'), H—C(5")), 3.32 (t, 2H, $CH_2$-phenyl), 2.74 (m, 1H, H—C(2')), 2.32 (m, 1H, H—C(2")); UV (ACN): pmax (nm)/log p: 262/4.34, 219/4.68; $C_{26}H_{22}N_6O_8$ (546.50); calc: C, 57.14, H, 4.06, N, 15.38 ; found: C, 57.27, H, 4.37, N, 15.11.

4.2 5'-O-Dimethoxytrityl-O$^6$-[2-(4-nitrophenyl)ethyl]N$^2$-phthaloyl-2'-deoxyguanosine Synthesis takes place in accordance with Example 1.2: 990 mg of O$^6$-[2-(4-nitro-phenyl)ethyl]-N$^2$-phthaloyl-2'-deoxyguanosine (1.81 mmol) are dissolved in 25 ml of pyridine, 674 mg of 4,4-dimethoxytrityl chloride (1.99 mmol) are added and the mixture is stirred for 3 hr. It is extracted with 100 ml of AcOEt and 100 ml of a saturated solution of sodium hydrogen carbonate. Chromatography subsequently takes place on silica gel (25 g of $SiO_2$) in a toluene/AcOEt gradient (20–66% AcOEt), and 1.00 g (1.18 mmol; 67%) of a white foam is obtained.

TLC (silica gel): $R_f$=0.57 (toluene/AcOEt 1:6); $^1$H-NMR (DMSO, 250 MHZ): 8.59 (s, 1H, H—C(8)), 8.13 (d, 2H, 2H o to $NO_2$), 8.00 (m, 4H, pth), 7.60 (d, 2H, 2H m to $NO_2$), 7.10–7.26 (m, 9H, DMTr), 6.68 (m, 4H, o to $OCH_3$), 6.43 (m, 1H, H—C(1')), 5.36 (d, 1H, HO—C($3^1$)), 4.81 (t, 2H, $CH_2$O), 4.46 (m, 1H, H—C(3')), 3.95 (m, 1H, H—C(4')), 3.67 (s, 6H, 2× O—$CH_3$), 3.32 (t, 2H, $CH_2$-phenyl), 3.05–3.25 (m, 2H, H—C(5'), H—C($5^{11}$)), 2.85 (m, 1H, H—C(2')), 2.38 (m, 1H, H—C(2")); UV (ACN): pmax (nm)/log p: 262/4.38, 218/4.78.

$C_{47}H_{40}N_6O_{10}$ (848.87); calc.: C, 66.50, H, 4.75, N, 9.90; found: C, 66.65, H, 4.90, N, 9.52.

4.3 5'-O-Dimethoxytrityl-O$^6$-[2-(4-nitrophenyl)ethyl]-N$^2$-phthaloyl-2'-deoxyguanosine-3'-O-(β-cyanoethyl-N,N-diisopropyl)phosphitamide Synthesis takes place in accordance with Example 1.3, but using pyridine hydrochloride instead of tetrazole; yield: 87%.

TLC (silica gel): $R_f$=0.74/0.82 (toluene/AcOEt 1:6)); $^1$H-NMR (DMSO, 250 MHZ): 8.63 (s, 1H, H—C(8)), 8.13 (s, 2H, 2H o to $NO_2$), 8.00 (m, 4H, pth), 7.61 (s, 2H, 2H m to $NO_2$), 7.08–7.24 (m, 9H, DMTr), 6.63–6.71 (m, 4H, DMTr), 6.45 (m, 1H, H—C(1')), 4.80 (m, 3H, H—C(3'), $CH_2$O), 4.10 (m, 1H, H—C(4')), 3.66 and 3.67 (2s, 6H, 2×

OCH$_3$), 2.95–3.59 (m, 10 H, NC—CH$_2$O, H—C(5'), H—C (5"), 2× N—CH, CH$_2$CN, CH$_2$-phenyl)2.72 (m, 1H, H—C (2')), 2.61 (m, 1H, H—C(2")), 0.90–1.20 (m, 12 H, 2× C(CH$_3$)$_2$); $^{31}$P-NMR (DMSO, 161.7 MHZ): 2s 148.55/ 148.05; C$_{56}$N$_{57}$N$_8$O$_{11}$P$_1$ (1049.09); calc.: C, 64.11, H, 5.48, N, 10.68; found: C, 63.92, N, 5.47, H, 10.12.

EXAMPLE 5

5'-O-Dimethoxytrityl-O$^6$-[2-(phenylsulfonyl)ethyl]-N$^2$-phthaloyl-2'-deoxyguanosine-3'-(cyanoethyl-N, N-diisopropyl)phosphitamide 5.1 O$^6$-[2-(Phenylsulfonyl)ethyl]-N$^2$-phthaloyl-2'-deoxyguanosine The synthesis is effected in accordance with Example 1.1.
Variation A: Elimination of the Trimethylsilyl Groups With Pyridine/Water 300 mg of O$^6$-[2-(Phenylsulfonyl)ethyl]-2'-deoxyguanosine (0.69 mmol) are stirred together with 0.22 ml of chlorotrimethylsilane (1.7 mmol) in 10 ml of pyridine and, after 30 min, 0.14 ml of phthaloyl chloride (0.97 mmol) in 2 ml of dry dioxane is added dropwise within a period of 7 min. After 1 hr, the reaction is stopped with water and the mixture is then stirred for a further 15 min. It is extracted twice with 25 ml of water and 25 ml of dichloromethane, and the aqueous phases are extracted once again with 25 ml of dichloromethane. Purification is effected on a silica gel column (7 g of SiO$_2$) by means of flash chromatography in a petroleum ether/acetone gradient (50–66% acetone). 0.14 g (0.24 mmol; 36%) of a virtually colorless foam is obtained.
Variation B: Elimination of the Trimethylsilyl Groups With Ammonium Fluoride 0.87 g of O$^6$-[2-(Phenylsulfonyl)ethyl]-2'-deoxyguanosine (2 mmol) is stirred together with 0.56 ml of chlorotrimethylsilane (4.4 mmol) in 15 ml of dry acetonitrile and 1.03 ml of pyridine and, after 30 min, 0.29 ml of phthaloyl chloride (2 mmol) is added dropwise. After 35 min, the mixture is subjected to rotary evaporation and the residue is coevaporated with toluene and treated with 160 mg of ammonium fluoride (4.3 mmol) in 25 ml of MeOH. This mixture is stirred for 3 min and extracted twice with 100 ml of a solution of sodium hydrogen carbonate and 100 ml of dichloromethane, and the aqueous phases are extracted once again with 50 ml of dichloromethane. Purification is effected on a silica gel column (25 g of SiO$_2$) by means of flash chromatography in a petroleum ether/acetone gradient (30–75% acetone). 0.45 g (0.79 mmol; 40%) of a slightly yellowish foam is obtained.

TLC (silica gel): R$_f$=0.27 (petroleum ether/acetone 1:2); $^1$H-NMR (DMSO, 250 MHZ): 8.65 (s, 1H, H—C(8)), 7.96–8.7 (m, 4H, pth), 7.82 (m, 2H, o to SO$_2$), 7.36–7.49 (m, 3H, 2H m to SO$_2$, 1H p to SO$_2$), 6.37 (t, 1H, H—C(1')), 5.32 (d, 1H, HO—C(3')), 4.92 (t, 1H, HO—C(5')), 4.80 (t, 2H, CH$_2$O), 4.41 (m, 1H, H—C(3')), 4.12 (t, 2H, CH$_2$SO$_2$), 3.86 (m, 1H, H—C(4')), 3.45–3.65 (m, 2H, H—C(5'), H—C(5")), 2.72 (m, 1H, H—C(2')), 2.33 (m, 1H, H—C(2")); UV (ACN): pmax (nm)/log p: [294/3.50], 259/4.26, 219/4.73; C$_{26}$H$_{23}$N$_5$O$_8$S$_1$×H$_2$O (583.58) calc.: C, 53,51; H, 4,32; N, 12,00; found: C, 53,95; H, 4,45; N, 11,72.

5.2 5'-O-Dimethoxytrityl-O$^6$-[2-(phenylsulfonyl)ethyl]-N$^2$-phthaloyl-2'-deoxyguanosine Synthesis takes place in accordance with Example 1.2: 560 mg of O$^6$-[2-(phenylsulfonyl)ethyl]-N$^6$-phthaloyl-2'-deoxyguanosine (1 mmol) in 20 ml of pyridine are stirred for 16 hr together with 373 mg of 4,4-dimethoxytrityl chloride (1.1 mmol). The mixture is extracted with 100 ml of dichloromethane and 100 ml of a saturated solution of sodium hydrogen carbonate. Chromatography subsequently takes place on silica gel (20 g of SiO$_2$) in a toluene/AcOEt gradient (30–80% AcOEt), and 570 mg (0.66 mmol; 66%) of a slightly. yellowish foam are obtained.

TLC (silica gel): R$_f$=0.39 (toluene/AcOEt/MeOH 5:4:1); $^1$H-NMR (DMSO, 250 MHZ): 8.55 (s, 1H, H—C(8)), 8.01–8.07 (m, 4H, pth), 7.82 (m, 2H, 2H o to SO$_2$), 7.32–7.38 (m, 3H, 2H m to SO$_2$, 1H p to SO$_2$), 7.05–7.27 (m, 9H, DMTr), 6.67–6.73 (m, 4H, o to OCH$_3$), 6.41 (m, 1H, H—C(1')), 5.37 (d, 1H, HO—C(3')), 4.79 (t, 2H, CH$_2$O), 4.46 (m, 1H, H—C(3')), 4.10 (t, 2H, CH$_2$SO$_2$), 3.96 (m, 1H, H—C(4')), 3.68 (s, 6H, 2× OCH$_3$), 3.09–3.25 (m, 2H. H—C(5'), H—C(5")), 2.81 (m, 1H, H—C(2')), 2.35 (m, 1H, H—C(2")); UV (ACN): pmax (nm)/log p: 261/4.26, 217/ 4.80; C$_{47}$H$_{41}$N$_5$O$_{10}$S$_1$ (867.93); calc.: C, 65.04, H, 4.76, N, 8.07; found: C, 64.97, H, 4.82, N, 7.88.

5.3 5'-O-Dimethoxytrityl-O$^6$-[2-(phenylsulfonyl)ethyl]-N2-phthaloyl-2$^1$-deoxyguanosine-3'-O-(cyanoethyl-N,N-diisopropyl)phosphitamide Synthesis takes place in accordance with Example 2: 470 mg of 5'-O-dimethoxytrityl-O$^6$-[2-(phenylsulfonyl)ethyl]-N-phthaloyl-2'-deoxyguanosine (0.54 mmol) are dissolved in 8 ml of acetonitrile, and 196 mg of bis(N,N-diisopropylamino)-2-cyanoethoxyphosphane (0.65 mmol) and 0.54 ml of an 0.5 M solution of pyridinium chloride are added. After 3 hr, a further 150 mg of phosphane and 0.27 ml of pyridinium chloride solution are added and the mixture is stirred for a further 3.5 hr. It is extracted with 50 ml of dichloromethane and 50 ml of a solution of sodium hydrogen carbonate. Chromatography is carried out in a toluene/ethyl acetate gradient (33–50% AcOEt), and 420 mg (0.39 mmol; 73%) of a white foam are obtained.

TLC (silica gel): R$_f$=0.49/0.60 (petroleum ether/AcOEt/ triethylamine 1:9:1)); $^1$H-NMR (DMSO, 250 MHZ): 8.57 (2s, $^1$H, H—C(8)), 7.98–8.03 (m, 4H, pth), 7.81 (m, 2H, 2H o to SO$_2$), 7.31–7.40 (m, 3H, 2H m to SO$_2$, 1H o to SO$_2$), 7.08–7.25 (m, 9H, DMTr), 6.39–6.73 (m, 4H, DMTr), 6.43 (m, 1H, H—C(1')), 4.78 (m, 3H, H—C(3'), CH$_2$O), 4.10 (m, 3H, CH$_2$SO$_2$, H—C(4')), 3.66 and 3.67 (2s, 6H, 2× OCH$_3$), 3.30–3.60 (m, 4 H, NC—CH$_2$O, 2× N—CH), 3.23 (m, 2H, H—C(5'), H—C(5")), 3.00 (m, 1H, H—C(2')), 2.62 and 2.73 (2t, 2H, CH$_2$CN), 2.50 (m, 1H, H—C(2")), 0.86–1.19 (m, 12 H, 2' C(CH$_3$)$_2$); $^{31}$P-NMR (DMSO, 161.7 MHZ): 2s 148.54/ 148.06; C$_{56}$H$_{58}$N$_7$O$_{11}$P$_1$S$_1$ (1068.15); calc.: C, 62.97, H, 5.47, N, 9.18; found: C, 62.25, N, 5.65, H, 8.82.

EXAMPLE 6

5'-O-Dimethoxytrityl-N$^6$-phthaloyl-3'-O-succinoyl-2'-O-deoxyadenosine 342 mg of 5'-O-dimethoxytrityl-N$^6$-phthaloyl-2'-O-deoxyadenosine (Example 1.2) (0.5 mmol) are dissolved in 10 ml of absolute dichloromethane, and 79 mg of 4,4-dimethylaminopyridine (0.65 mmol) and 100 mg of succinic anhydride (1 mmol) are added. After 17 hr, the mixture is diluted with 50 ml of dichloromethane and extracted with 30 ml of a saturated solution of sodium hydrogen carbonate and then 10% citric acid. After drying the organic phase over MgSO$_4$ and subjecting it to rotary evaporation, and drying the residue under high vacuum, 390 mg (0.49 mmol; 98%) of a white foam are obtained.

TLC (silica gel): R$_f$=0.17 (toluene//AcOEt/MeOH 5:4:1)); $^1$H-NMR (DMSO, 250 MHZ): 12.30 (s, 1H, COOH), 8.91 (s, 1H, H—C(2)), 8.82 (s, 1H, H—C(8)), 8.06 (m, 4H, pth), 7.17 (m, 9H, DMTr), 6.83 (m, 4H, o to OCH$_3$), 6.56 (t, 1H, H—C(1')), 5.45 (m, 1H, H—C(3')), 4.25 (m, 1H, H—C(4')), 3.70 (s, 6H, 2× O—CH$_3$), 3.33 (m, 2H, H—C (5'), H—C(5'')), 2.58 (m, 6H, H—C(2'), H—C(2''), CH$_2$CH$_2$); UV (ACN): pmax (nm)/log p: [300/3.60], 271/4.17, [220/4.72]; C$_{43}$H$_{37}$N$_5$O$_{10}$×H$_2$O (801.82); calc.: C, 64.41, H, 4.90, N, 8.73; found: C, 64.47, H, 4.98, N, 8.74.

EXAMPLE 7

5'-O-Dimethoxytrityl-O$^6$-[2-(4-nitrophenyl)ethyl]-N$^2$-phthaloyl-3'-O-succinoyl-2'-O-deoxyguanosine 212 mg of 5'-O-Dimethoxytrityl-O$^6$-[2-(4-nitrophenyl) ethyl]-N$^2$-phthaloyl-2'-deoxyguanosine (0.25 mmol) are dissolved in 5 ml of absolute dichloromethane, and 50 mg of succinic anhydride (0.5 mmol) and 40 mg of 4,4-dimethylaminopyridine (0.32 mmol) are added. After the mixture has been stirred for 24 hr, it is diluted with 60 ml of dichloromethane and this mixture is extracted with 40 ml of a saturated solution of sodium hydrogen carbonate and then with 40 ml 10% citric acid solution. After the organic phase has been dried over magnesium sulfate, it is subjected to rotary evaporation and the residue is dried under high vacuum. 210 mg (0.22 mmol; 88%) of a slightly yellowish foam are obtained.

$^1$H-NMR (DMSO, 250 MHZ): 12.27 (s, 1H, COOH), 8.61 (s, 1H, H—C(8)), 8.14 (d, 2H, 2H o to NO$_2$), 7.96–8.05 (m, 4H, pth), 7.61 (d, 2H, 2H m to NO$_2$), 7.05–7.27 (m, 9H, DMTr), 6.65–6.71 (m, 4H, o to OCH$_3$), 6.44 (t, 1H, H—C (1')), 5.36 (m, 1H, H—C(3')), 4.82 (t, 2H, OCH$_2$), 4.14 (m, 1H, H—C(4')), 3.67 (s, 6H, 2× O—CH$_3$), 3.16–3.42 (m, 4H, H—C(5'), H—C(5''), CH$_2$-phenyl), 2.45–2.60 (m, 6H, H—C (2'), H—C(2''), CH$_2$CH$_2$); UV (ACN): pmax (nm)/log p: 262/4.37, 216/4.78.

EXAMPLE 8

8.1 Support-Derivatization of Long-Chain Methylaminoalkyl (LCMAA)-CPG 1 g of 1000 Å or 1400 Å CPG material is dried for 1.5 hours under high vacuum. 1 g of carbonyldiimidazole (12.4 mmol) is dissolved in 20 ml of dry dichloromethane, and the dried CPG support material is added and the whole is thoroughly mixed on a vibrator for 6 hours. The overlying solution is decanted off and digestion is carried out three times with dry dichloromethane. This is followed by taking up in 15 ml of dry dichloromethane, after which 1 ml of 1,6-bis(methylamino)hexane (5.8 mmol) is added. After 3 hours on the vibrator, the supernatant is decanted off and this is followed by filtering off with suction and washing consecutively with pyridine, DMF, methanol, acetone and diethyl ether. Drying then takes place under high vacuum.

8.2 Loading LCAMAA-CPG With Phthaloyl-Protected Succinates 400 mg of LCMAA-CPG are shaken with 7 mg TOTU (O-[(ethoxycarbonyl)cyanomethyleneamino]-N,N,N',N'-tetramethyluronium tetrafluoroborates: W. König, G. Breipohl, P. Pokorny, M. Birkner, *Proceedings of the 21st European Peptide Symposium* 1990, E. Giralt, D. Andreu, Eds., *ESCOM,* Leiden, p. 143) (21 µmol), 3 µl of N-methylmorpholine (27 µmol) and 23 µmol of nucleoside succinate for 2 hours in 5 ml of dry acetonitrile. Filtering off with suction takes place and the filter residue is washed consecutively with DMF, methanol, acetone and diethyl ether.

Capping

The nucleoside-loaded support is shaken for 0.5 hours with 10 mg of DMAP, 0.5 ml of acetic anhydride and 10 ml of pyridine. Filtering off with suction then takes place and the filter residue is washed consecutively with DMF, methanol, acetone and diethyl ether. In the case of 5'-O-dimethoxytrityl-O$^6$-[2-(4-nitrophenyl)ethyl]-N$_2$-phthaloyl-3'-O-succinyl-2'-deoxyguanosine, capping is effected using a mixture composed of 0.5 ml of N-methylimidazole, 0.5 ml of acetic anhydride and 5 ml of pyridine.

The following loadings are obtained:

| Support | Succinate | Loading [µmol/g] |
| --- | --- | --- |
| 1000 Å | dA$^{pth}$ | 8.9 |
| 1400 Å | dA$^{pth}$ | 12.5 |
| 1400 Å | dGP$^{pth/npe}$ | 10.9 |

8.3 Derivatizing LCMAA-CPG With Succinic Anhydride 500 mg of 1400 Å LCMAA-CPG are shaken for 24 hours in 4 ml of dry pyridine together with 12 mg of DMAP (0.1 mmol) and 400 mg of succinic anhydride. Filtering off with suction takes place and the filter residue is washed with pyridine and dichloromethane.

Loading the Succinyl-LCMAA-CPG With Phthaloyl-Protected 5'-O-DMTr-nucleosides 3 ml of dry pyridine and 12 µl of triethylamine are added to 150 mg of succinylated LCMAA-CPG, 1.8 mg of DMAP (0.015 mmol), 29 mg of 1-(3-dimethyl-aminopropyl) ethylcarbodiimide (0.15 mmol) and 0.015 mmol of 5'-O-DMTr-protected phthaloyl compound. The mixture is shaken for 24 hours, after which 20 mg of pentachlorophenol (0.07 mmol) are added and the whole is shaken for a further 23 hours. 0.75 ml of piperidine is then added and filtering off with suction takes place immediately after 5 minutes and the filter residue is washed consecutively with dichloromethane and diethyl ether.

Capping: the nucleoside-loaded support is shaken for 1.5 hours with a mixture composed of 0.5 ml of N-methylimidazole, 0.5 ml of acetic anhydride and 5 ml of pyridine and subsequently washed with DMF, methanol, acetone and diethyl ether.

The following loadings are obtained:

| Support | 5'-O-DMTr-nucleoside | Loading [µmol/g] |
| --- | --- | --- |
| 1400 Å | dC$^{pth}$ | 2.2 |
| 1400 Å | dG$^{pth/npe}$ | 3 |

EXAMPLE 9

Oligonucleotide Synthesis

Unmodified oligonucleotides were synthesized on an automated DNA synthesizer (Applied Biosystems Model 392) using the standard phosphoramidite synthesis cycle. The phthaloyl strategy makes possible either use of the water-containing oxidation mixture iodine/pyridine/THF/water or water-free oxidation using tert-butyl hydroperoxide in acetonitrile. The oxidation times are 15 seconds for iodine and 90 seconds for tert-butyl hydroperoxide. After the synthesis cycles have been completed, the protecting groups are eliminated, while the oligonucleotide is still on the support, with DBU in N-methyimidazole or acetonitrile (see below) (DBU: 1,8-diazobicyclo[6.4.0]undec-7-ene) over a period of from 15 minutes to 12 h. The oligonucleotide, which is now free of all protecting groups, is then released from the support by treating with concentrated aqueous ammonia (25%). The oligonucleotide is now present in highly pure form in ammoniacal solution and is obtained by lyophilizing the ammoniacal solution. In the phthaloyl strategy, in contrast to the acyl strategy, there is no necessity for an additional purification by HPLC or PAGE for the purpose of removing the protecting groups.

The following sequences were synthesized using the phosphoramidites described in Examples 1–5 and the derivatized solid supports described in Example 8. In the individual sequences, the conditions described for eliminating the protecting groups were varied successfully.

| Sequence | Ox | Phthaloyl elimination | | | other times |
|---|---|---|---|---|---|
| | | 12 hr | 1 hr | 0.5 hr | |
| 5'-A$_5$ | B | (1) | (1) | | 3 hr$^{(1)}$ |
| 5'-A$_6$ | I | (1) | | | |
| 5'-A$_7$ | I | (1) | | | |
| 5'-A$_8$ | B | | | | 25 min$^{(1)}$ |
| 5'-A$_9$ | B | (1) | | | 15 min/3 hr (1) |
| 5'-A$_{15}$ | B | (1) | (1) | | |
| 5'-A$_{20}$ | B | (1) | | | |
| 5'-CCC CCC CT | B | (2) | | | 25 min$^{(1)}$ |
| 5'-CCC CAT TAT | B | | | | 25 min$^{(1)}$ |
| 5'-AAT CCTA | B | | | | 12 min$^{(1)}$ |
| 5'-ATT CCTA | B | | | | 12 min$^{(1)}$ |
| 5'-ATT TAA TTT AAT TTAA (SEQ ID NO:1) | B | (1) | | | |
| 5'-GCC TCT GAA CCT CTT CAG CA (SEQ ID NO:2) | I | (1) | | (3) | |
| 5'-TTA CTA ATC AGA ATG TCT CTC A (SEQ ID NO:3) | I | (1) | (3) | (3) | |
| 5'-GTT GGG TCC GAA TAT TTC AGA A (SEQ ID NO:4) | B | (1) | | (3) | |

Abbreviations: oxidizing agents
(Ox): I= iodine; B= tert-butyl hydroperoxide;
phthaloyl elimation: $^{(1)}$= 1 M DBU/ACN; $^{(2)}$= 2 M DBU/ACN; $^{(3)}$= 2 M DBU in N-methylimidazole The following sequences were synthesized using the phosphoramidites described in Examples 1–5 and the solid supports described in Example 8. In this case, a solution of 0.5 M pyridine hydrochloride in acetonitrile was employed as the activator instead of tetrazole, with condensation times of from 12 to 30 seconds. In the individual sequences, the conditions described for eliminating the protecting groups were varied successfully.

| Sequence | Ox | Co | Phthaloyl elimination | | |
|---|---|---|---|---|---|
| | | | 12 hr | 1 hr | 0.5 hr |
| 5'-A$_6$ | B | 12 | (1) | | |
| 5'-GGG t | I | 30 | (1) | | (2) |
| 5'-GCC TCT GAA CCT CTT CAG CA (SEQ ID NO: 2) | I | 24 | (1) | | |
| 5'-TTA CTA ATC AGA ATG TCT CTC A (SEQ ID NO: 3) | I | 24 | (1) | (3) | (3) |
| 5'-GTT GGG TCC GAA TAT TTC AAG A (SEQ ID NO: 5) | I | 24 | (1) | | (3) |
| 5'-GCT GCA TG | I | 24 | | | (3) |
| 5'-CCT CCA ATC TAG (SEQ ID NO: 6) | I | 30 | (1) | (3) | |
| 5'-TGT AGT AGT GGT (SEQ ID NO: 7) | I | 30 | (1) | (3) | |
| 5'-GTT ATT | I | 30 | (1) | (3) | |
| 5'-TGA CGT TAT T (SEQ ID NO: 8) | I | 30 | (1) | (3) | |

Abbreviations:
oxidizing agents (Ox): I = iodine; B = tert-butyl hyproperoxide;
Condensation time (Co): in seconds;
phthaloyl elimination: (1) = 1M DBU/ACN; (2) = 2M DBU/ACN; (3) = 2M DBU in N-methylimidazole The high purity of the oligonucleotides (>95%) was confirmed by HPLC.

HPLC: Gradient: (reversed phase; RP 18); flow rate 1 ml/min

Solution A: 0.1 N TEAAC pH 7

Solution B: 0.1 N TEAAc: AcCN 1:1

| Step | Min | Vol. % | Vol. % |
|---|---|---|---|
| 1 | 0 | 95 | 5 |
| 2 | 2 | 95 | 5 |
| 3 | 32 | 60 | 40 |
| 4 | 45 | 0 | 100 |
| 5 | 50 | 95 | 5 |
| 6 | 55 | 95 | 5 |

It will be apparent to those skilled in the art that various modifications and variations can be made to the methods and oligonucleotides of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 19627898.8, including its figures, claims, and abstract, for which benefit of priority under 35 USC § 119 is claimed, is expressly incorporated herein in its entirety.

What is claimed is:

1. A process for preparing an oligonucleotide on a solid support comprising protecting exocyclic amino group(s) of a nucleobase which are present with a cyclic diacyl group, coupling the nucleobase to the solid support, sequentially linking the nucleobase to other nucleobase(s), in which exocyclic amino groups which are present on the nucleobase (s) being protected by a cyclic diacyl group to form a protected oligonucleotide, and deprotecting said protected oligonucleotide in the presence of a strong, nonnucleophilic base in an organic solvent.

2. The process as claimed in claim 1, wherein the protected oligonucleotide, which is bound to the solid support, is deprotected at a temperature ranging from 0 to 70° C. and for a time ranging from 0.1 to 16 h with a 0.1 to 5 M solution of diazabicyclo[5.4.0]undec07-ene.

3. The process as claimed in claim 1, wherein the protected oligonucleotide, which is bound to the solid support, is deprotected at a temperature ranging from 10 to 40° C. and for a time ranging from 0.1 to 2 h with a 0.3 to 3 M solution of diazabicyclo[5.4.0]undec07-ene.

4. The process as claimed in claim 1, wherein the protected oligonucleotide, which is bound to the solid support, is deprotected at a temperature ranging from 20 to 30° C. and for a time ranging from 0.2 to 1.5 h with a 0.5 to 2.5 M solution of diazabicyclo[5.4.0]undec07-ene.

5. The process as claimed in claim 1, wherein the oligonucleotide is a compound of the formula I

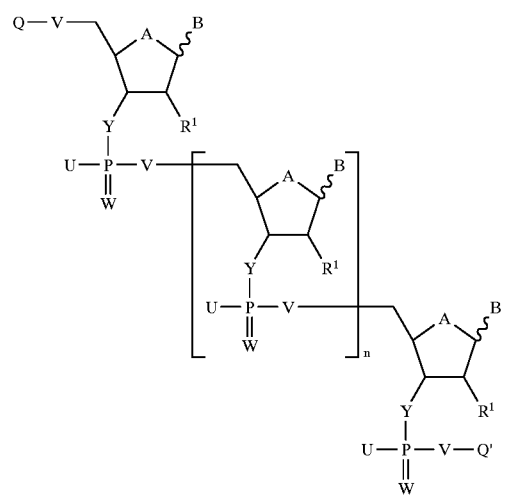

in which $R_1$ is, independently in each occurrence, hydrogen, hydroxyl, $C_1$–$C_4$-alkyl-O-$(CH_2CH_2O)_s$, in which s is a number from 1 to 3; O-allyl, halogen, azido, amino or $C_1$–$C_{18}$-alkoxy, which is optionally substituted one to three times by hydroxyl or $C_1$–$C_4$-alkoxy;

A is, independently in each occurrence, oxy, thioxy or methylene;

W is, independently in each occurrence, oxo, thioxo or selenoxo;

V is, independently in each occurrence, oxy, sulfanediyl or imino;

Y is, independently in each occurrence, oxy, sulfanediyl, imino or methylene;

B is a base, with at least one B being a base which possesses an exocyclic amino group;

n is an integer from 1 to 100;

U is, independently in each occurrence, hydroxyl, mercapto, $BH_3$, SeH, $C_1$–$C_{18}$-alkoxy, $C_1$–$C_{18}$-alkyl, $C_6$–$C_{20}$-aryl, ($C_6$–$C_{14}$)-aryl-($C_1$–$C_8$)-alkyl, $NHR^3$, $NR^3R^4$ or a radical of the formula II

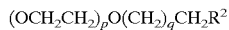
(II)

in which
p is an integer from 1 to 100;
q is an integer from 0 to 22;
$R^2$ is hydrogen or a functional group;

$R^3$ is $C_1$–$C_{18}$-alkyl, $C_6$–$C_{20}$-aryl, $C_6$–$C_{14}$-aryl-$C_1$–$C_8$-alkyl, or —$(CH_2)_c$—$[NH(CH_2)_c]_d$—$NR_5R_5$,
in which
c is an integer from 2 to 6,
d is an integer from 2 to 6 and
$R^5$ is, independently in each occurrence, hydrogen, $C_1$–$C_6$-alkyl or $C_1$–$C_4$-alkoxy-$C_1$–$C_6$-alkyl;

$R^4$ is $C_1$–$C_{18}$-alkyl, $C_6$–$C_{20}$-aryl or $C_6$–$C_{10}$-aryl-$C_1$–$C_8$)-alkyl, or, in the case of $NR^3R^4$, is, together with $R^3$ and the nitrogen atom carrying them, a 5–6-membered heterocyclic ring which can additionally contain a further heteroatom selected from the group consisting of O, S and N;

Q and Q' are, independently of each other, hydrogen or conjugates which contribute to the effect of antisense oligonucleotides or of triple helix-forming oligonucleotides, or Q and Q' are used as the label for a DNA probe, or, in the case where the oligonucleotide is designed to hybridize to a target nucleic acid, are conjugates which attack the target nucleic acid while binding or cross-linking;

wherein $R^1$ and the adjacent phosphoryl radical can be located either in the 2' and 3' positions or, conversely, in the 3' and 2' positions; each nucleotide can be present in its D or L configuration; the base B can be located in the alpha or beta position; the oligonucleotide may contain 3'—3'- or 5'—5' inversions;

and wherein (a) a compound of the formula III (III)

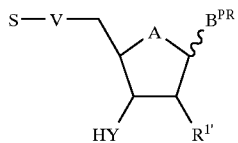

in which A, Y and V are defined as above, and
$R^{1'}$ is defined as $R^1$ except that when $R^1$ is hydroxyl or amino, $R^{1'}$ is a correspondingly protected hydroxyl or amino group,
S is a 5' protecting group which can be eliminated under acid conditions;
$B^{PR}$ is a natural or unnatural nucleobase in which any exocyclic amino groups which may be present are protected by a cyclic diacyl group;

is reacted with a compound of the formula IV (IV)

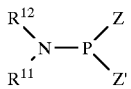

in which
Z' is $OR^{13}$, $C_1$–$C_{18}$-alkyl, $C_1$–$C_{18}$-alkoxy, $C_6$–$C_{20}$-aryl, or $C_6$–$C_{14}$-aryl-$C_1$–$C_8$-alkyl;
$R^{13}$ is a protecting group which can be eliminated with a strong, nonnucleophilic base;
$R^{11}$ and $R^{12}$ are identical or different and are $C_1$–$C_8$-alkyl, $C_5$–$C_{12}$-cycloalkyl, benzyl, or phenyl, or, together with the nitrogen atom to which they are bonded, a saturated or unsaturated heterocyclic ring optionally having additional heteroatoms;
Z is chlorine or bromine or a radical of the formula $NR^{11}R^{12}$, where $R^{11}$ and $R^{12}$ are defined as above;
in the presence of a base or, when Z is a radical of the formula $NR^{11}R^{12}$, then in the presence of a compound of the formula $[HNR^{14}R^{15}R^{16}]^{(+)} A^{(-)}$,
where $R^{14}$, $R^{15}$ and $R^{16}$ are identical or different and are a $C_1$–$C_4$-alkyl group and A is fluorine, chlorine or bromine;
or tetrazole or 5-($C_1$–$C_4$-alkylthio)-1H-tetrazole, to form a compound of the formula V (V)

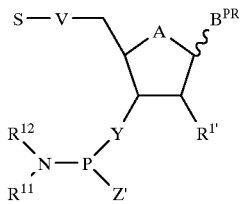

in which S, V, Y, A, $B^{PR}$, Z', $R^{1'}$, $R^{11}$ and $R^{12}$ are as defined above;

(b) compounds of the formula III are reacted with 1 to 10 equivalents of a linker in an organic solvent, optionally after adding a catalyst, to give a compound of the formula VI (VI)

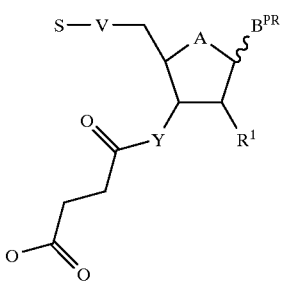

where S, V, Y, A, $B^{PR}$ and $R^1$ are defined as above, and reacted with the succinic acid residue in the 3' position serving as the linker to the solid support;

(c) the compound of the formula VI is coupled to a solid support SS in a solvent to obtain a compound of formula VII;

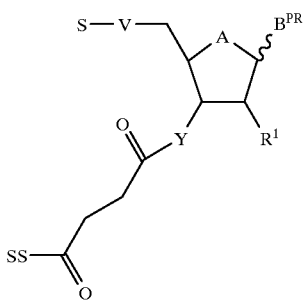

(d) the 5' protecting group is eliminated from VII;
(e) the resulting compound is reacted with a compound of the formula V in an organic solvent in the presence of a compound of the formula $[HNR^{14}R^{15}R^{16}]^{(+)} A^{(-)}$, which is defined as above, or tetrazole, 5-($C_1$–$C_4$-alkylthio)-1H-tetrazole or 5-($C_6$–$C_{12}$-aryl)-1H-tetrazole; and
(f) the resulting compound is oxidized optionally in the presence of additional organic solvent(s);
(g) the reaction steps (d)-(f) are repeated until the desired structure and chain length have been obtained;
(h) the compound which has been obtained in this way is deprotected by treating with diazabicyclo[5.4.0]undec-7-ene in an organic solvent; and
(i) the oligonucleotide is cleaved from the solid support.

6. The process as claimed in claim 5 wherein

U is, independently in each occurrence, hydroxyl, mercapto, $BH_3$, SeH, $C_1$–$C_6$-alkoxy, $C_1$–$C_6$-alkyl, $C_6$–$C_{20}$-aryl, ($C_6$–$C_{14}$)-aryl-($C_1$–$C_8$)-alkyl, $NHR^3$, $NR^3R^4$ or a radical of the formula II

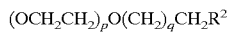

$(OCH_2CH_2)_pO(CH_2)_qCH_2R^2$ (II)

in which
p is an integer from 3 to 10;
q is an integer from 0 to 15;
$R^3$ is $C_1$–$C_8$-alkyl, $C_6$–$C_{20}$-aryl, $C_6$–$C_{14}$-aryl-$C_1$–$C_8$-alkyl, or —$(CH_2)_c$—$[NH(CH_2)_c]_d$—$NR^5R^5$,
in which
c is an integer from 2 to 6,
d is an integer from 0 to 6 and
$R^4$ is $C_1$–$C_8$-alkyl, $C_6$–$C_{20}$-aryl or $C_6$–$C_{10}$-aryl-$C_1$–$C_8$)-alkyl, or, in the case of $NR^3R^4$, is, together with $R^3$ and the nitrogen atom carrying them, a 5–6-membered heterocyclic ring which can additionally contain a further heteroatom selected from the group consisting of O, S and N;
Z' of formula (IV) is $OR^{13}$, $C_1$–$C_6$-alkyl, $C_1$–$C_6$-alkoxy, $C_6$–$C_{20}$-aryl, or $C_6$–$C_{14}$-aryl-$C_1$–$C_8$-alkyl;
$R^{11}$ and $R^{12}$ of formula (IV) are identical or different and are isopropyl, $C_5$–$C_8$-cycloalkyl, benzyl or phenyl or, together with the nitrogen atom to which they are bonded form a morpholine which may be substituted by one or more OC(O)O—$C_1$–$C_4$-alkyl esters;
the base of step (a) is pyridine, or a mixture of tetrahydrofuran (THF), dioxane, dichloromethane (DCM), chloroform, and/or acetonitrile with trimethylamine, triethylamine or diisopropylethylamine.

7. The process as claimed in claim 6, wherein, $R^5$ is, independently in each occurrence, hydrogen, $C_1$–$C_6$-alkyl or methoxyethyl;

$R^4$ is $C_1$–$C_4$-alkyl, $C_6$–$C_{20}$-aryl or $C_6$–$C_{10}$-aryl-$C_1$–$C_8$)-alkyl, or, in the case of $NR^3R^4$, is, together with $R^3$ and the nitrogen atom carrying them, a 5–6-membered heterocyclic ring which can additionally contain a further heteroatom selected from the group consisting of O, S and N;

$R^2$ is hydrogen or a functional group selected from the group consisting of hydroxyl, amino, $NHR^6$, COOH, $CONH_2$, $COOR^7$, and halogen, in which $R^6$ is $C_1$–$C_4$-alkyl, and
$R^7$ is $C_1$–$C_4$-alkyl;
and Z' of formula IV is $OR^{13}$.

8. The process as claimed in claim 6, wherein in step (a) a compound of the formula III, is reacted with a compound of formula IV in the presence of tetrazole or pyridine hydrochloride to form a compound of formula V;

in step (b) compounds of the formula III are reacted with from 1 to 2 equivalents of the linker;

in step (c) the compound of the formula VI is coupled to a solid support by reacting with N,N-dicyclohexylcarbodiimide and p-nitrophenol; and in step (e) the organic solvent is acetonitrile and the reaction takes place in the presence of tetrazole or pyridine hydrochloride.

9. The process as claimed in claim 5, wherein unreacted compounds from step (d) are deactivated by capping.

10. The process as claimed in claim 5, wherein, in compounds of the formulae (III), (V), (VI) and (VII), $B^{PR}$ is, independently in each occurrence,

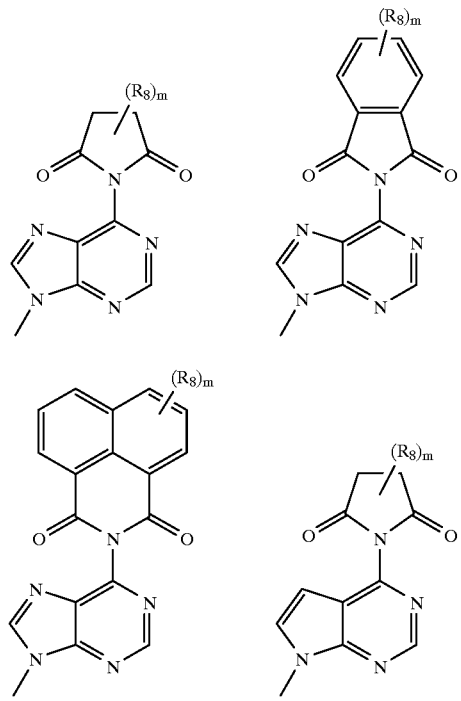

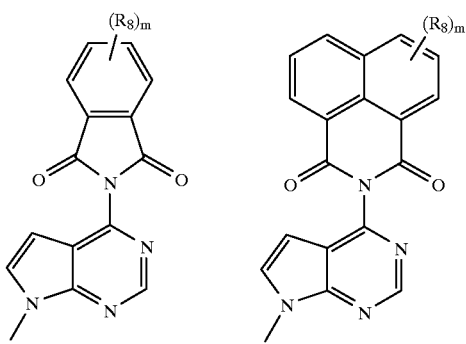
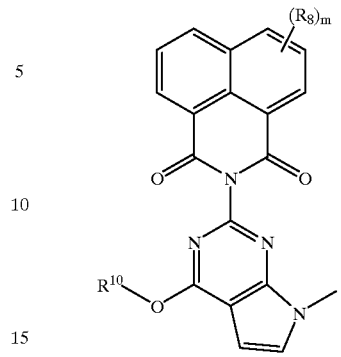
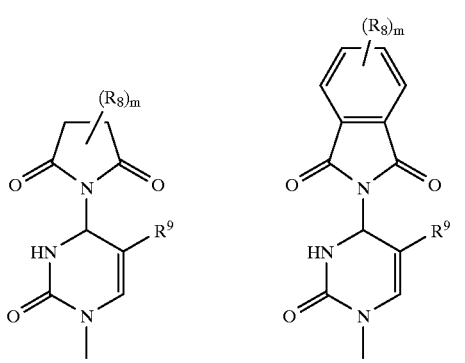
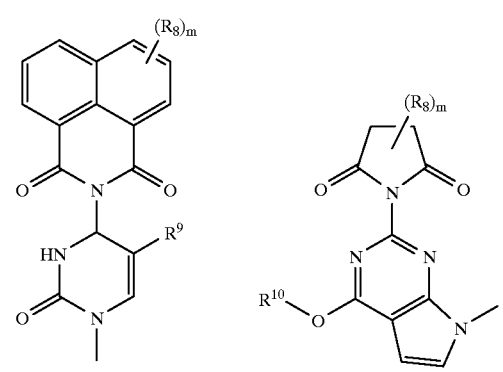
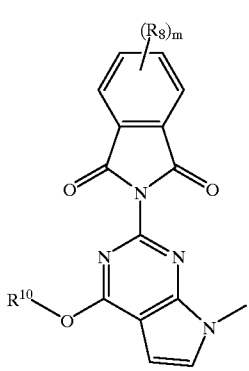
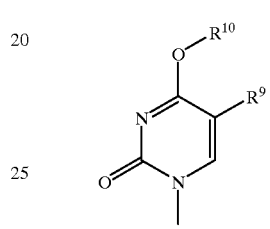

in which
m is a number from zero to four;
R⁸ is, independently in each occurrence, hydrogen, fluorine, chlorine, bromine, nitro, $C_1$–$C_4$-alkyl, $C_1$–$C_4$-alkoxy, or CN;
R⁹ is, independently in each occurrence, hydrogen, $C_1$–$C_6$-alkyl, $C_2$–$C_6$-(1-alkyne) or fluorine; and
R¹⁰ is, independently in each occurrence, hydrogen or a β-eliminatable protecting group.

11. The process as claimed in claim 5, wherein, in formula (I),
R¹ is hydrogen, hydroxyl, $C_1$–$C_4$-alkoxy or fluorine;
A is oxy;
W is oxo or thioxo;
V is oxy;
Y is oxy;
B is, independently in each occurrence, adenine, cytosine, guanine, uracil, thymine, 5-propyneuracil, 5-propynecytosine, 5-hexyneuracil or 5-hexynecytosine;
n is an integer from 5 to 40;
U is hydroxyl, mercapto, $C_1$–$C_6$-alkoxy, $C_1$–$C_6$-alkyl, NR³R⁴ or NHR³, in which
R³ is $C_1$–$C_8$-alkyl or methoxyethyl,
R₄ is $C_1$–$C_8$-alkyl, $C_6$–$C_{20}$-aryl or ($C_6$–$C_{10}$)-aryl-($C_1$–$C_8$)-alkyl, or, in the case of NR³R⁴, is, together with R³ and the nitrogen atom carrying them, a 5–6-membered heterocyclic ring which can additionally contain a further heteroatom selected from the group consisting of O, S and N; and
Q and Q' are, independently of each other, hydrogen.

12. The process as claimed in claim 11, wherein
R¹ is hydrogen;
n is an integer from 5 to 30;

U is hydroxyl or $C_1$–$C_6$-alkyl; and

Q and Q' are hydrogen.

13. A compound of the formula V $$(V)$$

in which

R[1'] is, independently in each occurrence, hydrogen, $C_1$–$C_4$-alkyl-O—$(CH_2CH_2O)_{1-3}$, O-allyl, fluorine, chlorine, azido, a protected hydroxyl group or amino group; or $C_1$–$C_{18}$-alkoxy, optionally substituted one to three times by hydroxyl or $C_1$–$C_4$-alkoxy;

A is oxy, thioxy or methylene;

V is oxy, sulfanediyl or imino;

Y is oxy, sulfanediyl, imino or methylene;

S is a 5' protecting group which can be eliminated under acid conditions;

B[PR] is a natural or unnatural nucleobase having at least one exocyclic amino group, with the exocyclic amino group(s) being protected by a cyclic diacyl group;

Z' is OR[13], $C_1$–$C_{18}$-alkyl, $C_1$–$C_{18}$-alkoxy, $C_6$–$C_{20}$-aryl or $C_6$–$C_{14}$-aryl-$C_1$–$C_8$-alkyl;

R[11] and R[12] are identical or different and are $C_1$–$C_8$-alkyl, $C_5$–$C_{12}$-cycloalkyl, benzyl or phenyl, or, together with the nitrogen atom to which they are bonded, a saturated or unsaturated heterocyclic ring optionally having additional heteroatoms; and R[13] is para-nitrophenylethyl or 2-cyanoethyl.

14. The compound as claimed in claim 13 wherein R[11] and R[12] are isopropyl, $C_5$–$C_8$-cycloalkyl or, together with the nitrogen atom to which they are bonded form morpholine which may have one or more OC(O)O—$C_1$–$C_4$-alkyl ester substituents.

15. The compound as claimed in claim 13, in which B[PR] is

-continued

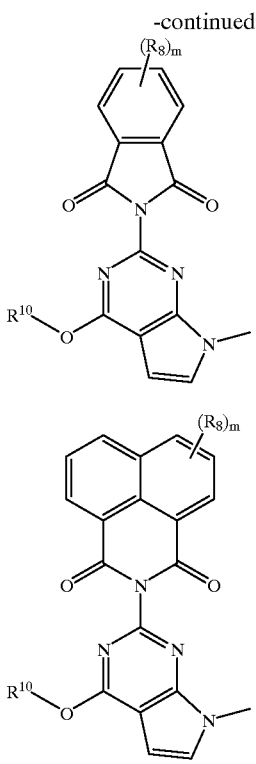

in which
m is a number from zero to four; and
R$^8$ is, independently in each occurrence, hydrogen, fluorine, chlorine, bromine, nitro, C$_1$–C$_4$-alkyl, C$_1$–C$_4$-alkoxy, or CN;
R$^9$ is, independently in each occurrence, hydrogen, C$_1$–C$_6$-alkyl, C$_2$–C$_6$-(1-alkyne)or fluorine; and
R$^{10}$ is, independently in each occurrence, hydrogen or a β-eliminatable Protecting group.

16. The compound as claimed in claim 15, wherein m is zero.

17. The compound as claimed in claim 13, wherein
R$^{1'}$ is hydrogen, a protected hydroxyl group, C$_1$–C$_4$-alkoxy or fluorine,
A is oxy;
V is oxy;
Y is oxy; and
Z' is OR$^{13}$, C$_1$–C$_6$-alkyl, C$_1$–C$_6$-alkoxy, C$_6$–C$_{20}$-aryl or C$_6$–C$_{14}$-aryl-C$_1$–C$_8$-alkyl.

18. The compound as claimed in claim 17, wherein Z' is OR$^{13}$.

19. A process for preparing a compound of the formula V

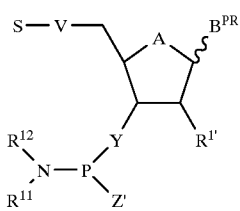

in which
R$^{1'}$ is, independently in each occurrence, hydrogen, C$_1$–C$_4$-alkyl—O—(CH$_2$CH$_2$O)$_{1-3}$, O-allyl, fluorine, chlorine, azido or a protected hydroxyl group or amino group; or C$_1$–C$_{18}$-alkoxy, optionally substituted one to three times by hydroxyl or C$_1$–C$_4$-alkoxy;
A is oxy, thioxy or methylene;
V is oxy, sulfanediyl or imino;
Y is oxy, sulfanediyl, imino or methylene;
S is a 5' protecting group which can be eliminated under acid conditions;
B$^{PR}$ is a natural or unnatural nucleobase having at least one exocyclic amino group, with the exocyclic amino group(s) being protected by a cyclic diacyl group;
Z' is OR$^{13}$, C$_1$–C$_{18}$-alkyl, C$_1$–C$_{18}$-alkoxy, C$_6$–C$_{20}$-aryl or C$_6$–C$_{14}$-aryl-C$_1$–C$_8$-alkyl;
R$^{11}$ and R$^{12}$ are identical or different and are C$_1$–C$_8$-alkyl, C$_5$–C$_{12}$-cycloalkyl, benzyl or phenyl, or, together with the nitrogen atom to which they are bonded, a saturated or unsaturated heterocyclic ring optionally having additional heteroatoms; and
R$^{13}$ is para-nitrophenylethyl or 2-cyanoethyl;
said process comprising reacting
a compound of the formula III

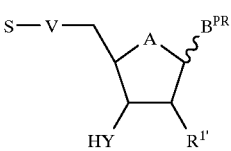 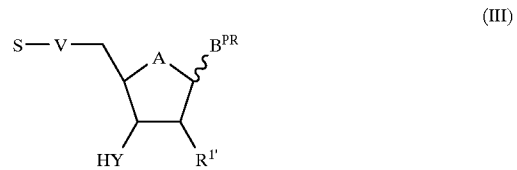 (III)

in which A, Y and V are defined as above, and
R$^{1'}$ is defined as R$^1$ except that when R$^1$ is hydroxyl or amino, R$^{1'}$ is a correspondingly protected hydroxyl or amino group,
S is a 5' protecting group which can be eliminated under acid conditions;
B$^{PR}$ is a natural or unnatural nucleobase in which any exocyclic amino groups which may be present are protected by a cyclic diacyl group;
is reacted with a compound of the formula IV

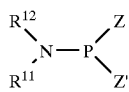 (IV)

in which
Z' is OR$^{13}$, C$_1$–C$_{18}$-alkyl, C$_1$–C$_{18}$-alkoxy, C$_6$–C$_{20}$-aryl, or C$_6$–C$_{14}$-aryl-C$_1$–C$_8$-alkyl;
R$^{11}$ and R$^{12}$ are identical or different and are C$_1$–C$_8$-alkyl, C$_5$–C$_{12}$-cycloalkyl, benzyl, or phenyl, or, together with the nitrogen atom to which they are bonded, a saturated or unsaturated heterocyclic ring optionally having additional heteroatoms;
R$^{13}$ is a protecting group which can be eliminated with a strong, nonnucleophilic base;
Z is chlorine or bromine or a radical of the formula NR$^{11}$R$^{12}$, where R$^{11}$ and R$^{12}$ are defined as above;
in the presence of a base, or, when Z is a radical of the formula NR$^{11}$R$^{12}$, then in the presence of a compound of the formula [HNR$^{14}$R$^{15}$R$^{16}$]$^{(+)}$ A$^{(-)}$,
where R$^{14}$, R$^{15}$ and R$^{16}$ are identical or different and are a C$_1$–C$_4$-alkyl group and A is fluorine, chlorine or bromine;

or tetrazole or 5-($C_1$–$C_4$-alkylthio)-1H-tetrazole, to obtain the compound of the formula V.

20. The process claimed in claim 19 wherein $R^{11}$ and $R^{12}$ are isopropyl, $C_5$–$C_8$-cycloalkyl or, together with the nitrogen atom to which they are bonded form morpholine which may have one or more OC(O)O—$C_1$–$C_4$alkyl ester substituents.

21. The process as claimed in claim 19, in which $B^{PR}$ is

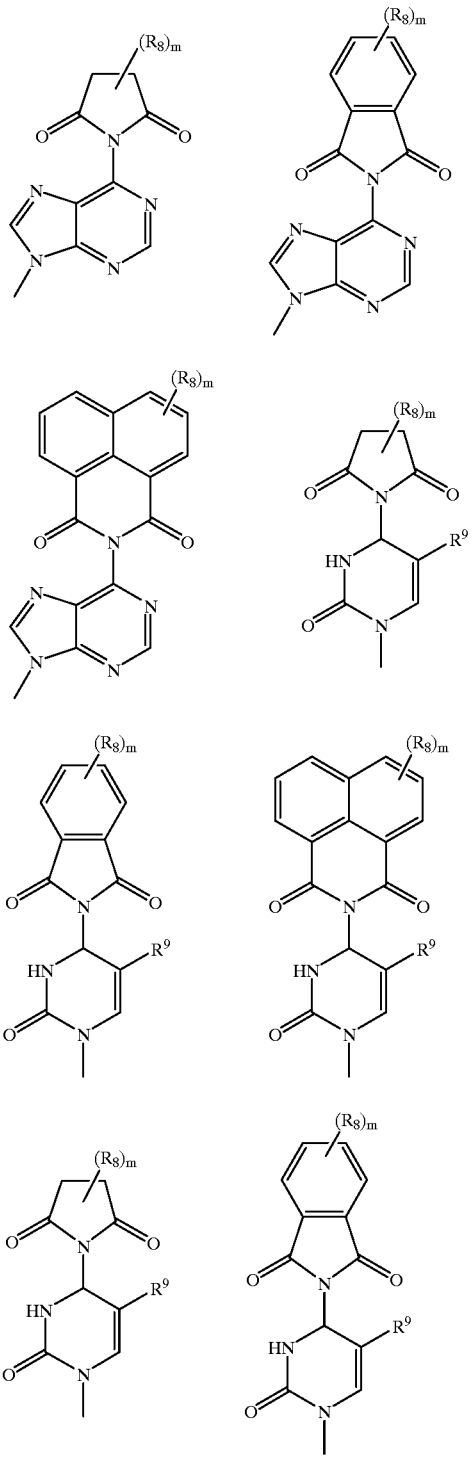

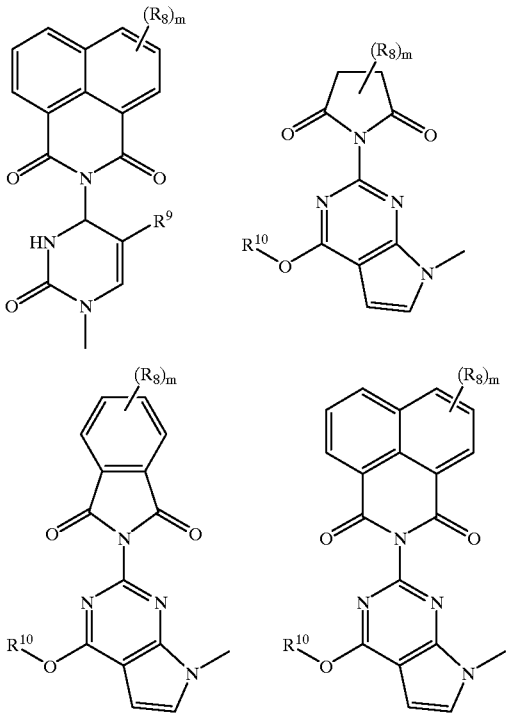

in which m is a number from zero to four; and $R^8$ is, independently in each occurrence, hydrogen, fluorine, chlorine, bromine, nitro, $C_1$–$C_4$-alkyl, $C_1$–$C_4$-alkoxy, or CN;

$R^9$ is, independently in each occurrence, hydrogen, $C_1$–$C_6$-alkyl, $C_2$–$C_6$-(1-alkyne)or fluorine; and $R^{10}$ is, independently in each occurrence, hydrogen or a β-eliminatable protecting group.

22. The process as claimed in claim 21, wherein m is zero.

23. The process as claimed in claim 19, wherein
   $R^{1'}$ is hydrogen, a protected hydroxyl group, $C_1$–$C_4$-alkoxy or fluorine,
   A is oxy;
   V is oxy;
   Y is oxy; and
   $Z^{1'}$ is $OR^{13}$, $C_1$–$C_6$-alkyl, $C_1$–$C_6$-alkoxy, $C_6$–$C_{20}$-aryl or $C_6$–$C_{14}$-aryl-$C_1$–$C_8$-alkyl.

24. The process as claimed in claim 23, wherein Z' is $OR^{13}$.

25. The process as claimed in claim 1, wherein the cyclic diacyl group is selected from the group consisting of phthaloyl, succinoyl, and naphthaloyl.

26. The compound as claimed in claim 13, wherein the cyclic diacyl group is selected from the group consisting of phthaloyl, succinoyl, and naphthaloyl.

27. The process as claimed in claim 19, wherein the cyclic diacyl group is selected from the group consisting of phthaloyl, succinoyl, and naphthaloyl.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (xi) SEQUENCE DESCRIPTION: SEQ ID NO:1:

ATTTAATTTA ATTTAA                                                        16

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:2:

GCCTCTGAAC CTCTTCAGCA                                                    20

(2) INFORMATION FOR SEQ ID NO:3:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:3:

TTACTAATCA GAATGTCTCT CA                                                 22

(2) INFORMATION FOR SEQ ID NO:4:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:4:

GTTGGGTCCG AATATTTCAG AA                                                 22

(2) INFORMATION FOR SEQ ID NO:5:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:5:

GTTGGGTCCG AATATTTCAA GA                                                 22

```
(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:6:

CCTCCAATCT AG                                                      12

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:7:

TGTAGTAGTG GT                                                      12

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:8:

TGACGTTATT                                                         10
```